United States Patent
Yao et al.

(10) Patent No.: US 12,286,620 B2
(45) Date of Patent: Apr. 29, 2025

(54) ANTIBODY LIBRARY CONSTRUCTION METHOD AND APPLICATION THEREOF

(71) Applicant: SHENZHEN ISTIRBIO CO., LTD., Guangdong (CN)

(72) Inventors: Yongchao Yao, Guangdong (CN); Youjia Li, Guangdong (CN); Sha Yin, Guangdong (CN); Guangjie Liu, Guangdong (CN)

(73) Assignee: SHENZHEN ISTIRBIO CO., LTD., Guangdong (CN)

( * ) Notice: Subject to any disclaimer, the term of this patent is extended or adjusted under 35 U.S.C. 154(b) by 968 days.

(21) Appl. No.: 16/973,722

(22) PCT Filed: Sep. 26, 2019

(86) PCT No.: PCT/CN2019/108128
§ 371 (c)(1),
(2) Date: Dec. 9, 2020

(87) PCT Pub. No.: WO2020/125120
PCT Pub. Date: Jun. 25, 2020

(65) Prior Publication Data
US 2021/0340523 A1    Nov. 4, 2021

(30) Foreign Application Priority Data
Dec. 21, 2018  (CN) .......................... 201811571758.5

(51) Int. Cl.
| C12N 15/10 | (2006.01) |
| C07K 16/28 | (2006.01) |
| C07K 16/30 | (2006.01) |
| C40B 30/04 | (2006.01) |

(52) U.S. Cl.
CPC ...... *C12N 15/1037* (2013.01); *C07K 16/2803* (2013.01); *C07K 16/303* (2013.01); *C40B 30/04* (2013.01)

(58) Field of Classification Search
None
See application file for complete search history.

(56) References Cited

U.S. PATENT DOCUMENTS

2016/0009813 A1    1/2016   Themeli et al.

FOREIGN PATENT DOCUMENTS

| CN | 108064283 A | 5/2018 | |
| CN | 108369230 A | 8/2018 | |
| CN | 108864290 A | 11/2018 | |
| CN | 109576292 A | 4/2019 | |
| JP | 2018525992 A | 9/2018 | |
| JP | 2018533920 A | 11/2018 | |
| WO | WO-2016138034 A1 * | 9/2016 | ............ A61K 35/17 |

OTHER PUBLICATIONS

ISR, dated Dec. 26, 2019, issued in corresponding International Patent Application PCT/CN2019/108128.
First Office Action, dated Aug. 29, 2022, issued in corresponding European Patent Application No. 19901269.1.
Rydzek, Julian et al., "Chimeric Antigen Receptor Library Screening Using a Novel NF-κB/NFAT Reporter Cell Platform," Molecular Therapy, vol. 27, No. 2, Feb. 2019, pp. 1-13.
Extended European Search Report, dated Nov. 10, 2021, issued in corresponding European Patent Application No. 19901269.1.
Notice of Reasons for Refusal, dated Nov. 16, 2021, issued in corresponding Japanese Patent Application No. 2021-517102.
First Office Action, dated Nov. 16, 2021, issued in corresponding Chinese Patent Application No. 201811571758.5.
Morsut, Leonardo et al., "Engineering Customized Cell Sensing and Response Behaviors Using Synthetic Notch Receptors," Cell, vol. 164, No. 4, Feb. 11, 2016, pp. 780-791.

* cited by examiner

*Primary Examiner* — Kaijiang Zhang
(74) *Attorney, Agent, or Firm* — Kathleen D. Rigaut; Howson & Howson LLP

(57) ABSTRACT

Disclosed by the present application are an antibody library construction method and an application thereof. The method comprises the following steps: inserting a first element and a second element into a same vector or different vectors, and transfecting the vectors into the cells to obtain an antibody expression cell library, i.e., the antibody library. The first element comprises CIS activators and selection marker genes; the second element comprises extracellular antibody library coding domain, Notch nuclear structure domain and intracellular transcription structure domain.

10 Claims, 12 Drawing Sheets

Specification includes a Sequence Listing.

ANTIBODY LIBRARY CONSTRUCTION METHOD AND APPLICATION THEREOF

CROSS REFERENCE OF RELATED APPLICATION

This application is a National Phase Entry of PCT/CN2019/108128 filed on Sep. 26, 2019 which claims priority to Chinese patent application No. 201811571758.5 filed on Dec. 21, 2018. Each of these applications is incorporated herein by reference as though set forth in full.

Incorporated herein by reference in its entirety is the Sequence Listing submitted via EFS-Web as a text file named SEQLIST.txt., created Jul. 6, 2021 and having a size of 82,818 bytes.

TECHNICAL FIELD

The present application belongs to the field of biotechnologies, and relates to an antibody library construction method and application thereof.

BACKGROUND

Antibodies are immunoglobulins which are expressed by B cells and bound to a particular antigen. In most animals, the antibody consists of paired heavy and light chains. Each chain is composed of two distinct regions, i.e., a variable region (Fv) and a constant region (Fc). The Fv regions of the heavy and light chains are responsible for binding to a target antigen, and are referred to as antigen binding determinants. An antibody in which the heavy chain variable region and light chain variable region of the antibody are linked via a short peptide (linker) of 15 to 20 amino acids is called a single chain antibody (scFv). The antibody drug dominates in the treatment of both tumor and autoimmune disease. Particularly, in the field of tumor therapy, the immunotherapy using monoclonal antibodies and antibody-drug conjugates based on monoclonal antibodies, bispecific antibodies, chimeric antigen receptor T (CAR-T) cells and the like is currently the most popular tumor therapy approach. Currently, various screening technologies for antibodies or antibody fragments are mainly developed based on the B cell monoclonal technology and the protein display technology.

The hybridism technology is the earliest technology used for establishing mouse B-cell monoclonality. B hybridoma cells can be obtained by fusing spleen cells of an animal immunized by a predetermined antigen with myeloma cells which are cultured in vitro and can grow indefinitely. Such hybridoma cells can proliferate indefinitely when cultured in vitro, as myeloma cells do, and can also synthesize and secrete specific antibodies as B lymphocytes do. A cell line of an individual hybridoma cell is obtained through monoclonality. Such a cell line produces an antibody that only targets the same antigenic epitope, and this antibody is called the monoclonal antibody. However, since murine antibodies are "heterologous" to humans, these monoclonal antibodies, when entering the human body, would induce the production of antibodies (i.e., human anti-mouse antibodies) against these antibodies. The human anti-mouse antibody neutralizes the murine antibody, rendering the murine antibody drug ineffective. The human-murine chimeric antibody is obtained by replacing the Fc segment of a murine antibody with the Fc segment of a human antibody, and the humanized antibody is obtained by further humanizing the FR segment of the Fv region of the chimeric antibody, thereby reducing the immunogenicity of the murine monoclonal antibody. The fully-humanized monoclonal antibody is one that is encoded by human genetic information completely, thereby avoiding the anti-heterologous protein reaction. Fusing the human B cell and the mouse myeloma cell expressing mIL-6 and hTERT to obtain the human-mouse hybridoma cell and transforming the human B cell with EBV to immortalize the human B cell both are effective means for developing fully-humanized monoclonal antibodies.

The monoclonal technology for B cells is time-consuming, labor intensive and inefficient, and is incapable of performing high throughput screening of antibodies. The protein display technology overcomes the defect that the hybridoma technology cannot carry out the high-throughput screening, and it can screen out target clones from a huge library (including more than $10^{10}$ independent clones). The commonly used protein display technology includes the phage display technology, bacterial display technology, ribosome display technology, yeast display technology, and mammalian cell display technology, which has been widely used for the screening of new antibodies and the improvement of antibody affinity.

The phage display technology has become the most widely used display technology due to its advantages of being capable of constructing large human antibody libraries relatively simply, robustly and conveniently. The phage display technology is to insert a coding gene of a polypeptide or protein into a proper position of a structural gene of a phage coat protein, and to make the exogenous polypeptide or protein and the coat protein fuse and express without affecting the normal function of other coat proteins, so that the exogenous polypeptide or protein and the coat protein are displayed on the surface of the phage. The polypeptide or protein displayed on the surface of the phage retains a relatively independent spatial structure and biological activity, and can recognize and bind to target molecules. A peptide library or a protein library displayed by the phage is bound to a fixed target molecule; the unbound phage is washed off, and the bound phage is eluted by acid or base or competitive molecules; *Escherichia coli* is infected by the neutralized phage for amplification; the proportion of the phage capable of specifically recognizing the target molecule gradually increases through 3-5 rounds of enrichment; and finally the polypeptide or protein that recognizes the target molecule is obtained. The genes of the antibody variable regions are inserted into a phage genome, and the expressed antibodies are displayed on the surface of the phage, thus a phage display antibody library is constructed, and antibodies against various antigens can be screened. Compared with the hybridoma technology, the approach of screening antibodies by using the phage display antibody library technology does not need immunization, and can reduce the antibody production period. This approach can also screen antibodies against antigens that have weak immunogenicity or exhibit toxicity in vivo, and has a wide application range. The phage display antibody library technology is not limited by species, and can construct antibody libraries of various species. The antibody screened from a human natural library can be directly used for antibody drug research without a humanization process. The phage display technology and the bacterial display technology are limited by the small capacity of the display system and are more suitable for displaying small peptides. Therefore, when the above technologies are used to display the antibody library, only fragments of the antibody can be displayed, and the intact antibody cannot be displayed. In addition, antibodies are eukaryotic proteins, and phages and bacteria cannot guarantee the complete and efficient expression of eukaryotic proteins.

The yeast display technology has become one of the most useful tools for screening human antibody libraries and for antibody affinity maturation. The most widely used yeast display system is the *Saccharomyces cerevisiae* Aga1p/2pα-lectin system, which links the GPI-anchored Aga1p protein to the displayed antibody relying on disulfide bonds. The yeast display technology has many advantages over the phage display technology, including an advantage of using a multi-color flow cytometry to quantify the intensity of antibody expression on the yeast surface as well as the intensity of binding to a fluorescently labeled antigen. The yeast can express secreted antibodies, which can help screen for clones with higher expression, better folding and proper secretion. The yeast display can accommodate all forms of antibodies and antibody fragments, including domain antibodies (dAbs), scFv, Fabs, and even IgG. However, the size of the yeast-displayed human antibody library was limited ($10^7$-$10^9$ independent clones) due to limitations in transformation efficiency and flow cytometry analysis technologies. However, the recently improved yeast electroporation transformation technology has improved transformation efficiency to $1.5 \times 10^8$ transformants/μg DNA, which is sufficient to construct an antibody library of up to $10^{10}$ independent clones.

The mammalian cell display technology has become the most important technology for the development of human antibodies. The folding, secretion and post-translational modification of proteins in mammalian cells are closest to those in human bodies. The mammalian cell display system is the most natural system for expressing and secreting human antibodies, and is beneficial to natural folding, stabilization and aggregation reduction of the antibodies. The mammalian cell display technology has similar advantages to the yeast display technology. It can analyze the antibody condition on the surface of mammalian cells by using the flow cytometry technology and sort cells with the optimal antibody expression signal. The mammalian cell display technology can display full-length human antibodies for the construction of antibody libraries of intact antibodies including the Fc fragment. However, the mammalian cell display technology has problems of low transfection efficiency and difficulty in increasing library capacity. Because of these limitations, the mammalian cell display technology was originally used for optimizing antibodies of relatively small libraries. In recent years, however, with advances in the technology, a large number of mammalian cell-based libraries have been established for antibody screening.

In addition to these mainstream antibody screening technologies, there are several distinct antibody screening technologies such as the growth signalobody-based antibody screening technology (Growth Signalobody), chimeric antigen receptor-based antibody screening technology (CAR-bodies) and deep sequencing antibody discovery technology, which all have great potential.

Owing to the advances in various antibody screening technologies and the further understanding of diseases, the discovery of numerous antigen targets enables the rapid development of antibody drugs. The therapeutic effect of antibodies and antibody-based drugs on tumors is closely related to the selected antigen targets, the number of antibody drug targets approved by the FDA is limited at present, and antibodies against these targets all are monoclonal antibodies or polyclonal antibodies with limited diversity mixed by multiple monoclonal antibodies.

The antibody drugs have good curative effects on tumor treatment. However, at present, no monoclonal antibody can completely solve the problem of tumor treatment, and the main reasons are as follows: (1) None of the currently identified tumor targets can completely cover a certain tumor. A certain tumor antigen may be highly expressed in a tumor cell, but it does not mean that this tumor antigen can be highly expressed in all tumor cells. Some tumor cells that do not express or express at a low level this tumor antigen may develop resistance to antibody drugs, resulting in rapid tumor relapse during the tumor therapy. (2) Few targets are expressed only in tumor cells and not in normal cells. Almost all tumor antigens are also expressed in some normal tissues of human, which causes damage to normal tissues by antibody drugs, resulting in great drug side effects. (3) The antigens of tumor cells have an extremely high mutation load, that is, the antigens have diversity and high mutation rate. The tumor cells have a large number of different tumor neoantigens. These tumor neoantigens are different even in the same tumor, and even if there is a determined tumor antigen, the mutation may still occur, resulting in the ineffectiveness of antibody drugs. (4) The targets that have been identified are limited, no effective target or combination of targets is available for many tumors, and a large number of unknown tumor targets have not been explored. The existing antibody screening technologies are basically used for screening monoclonal antibodies. The monoclonal antibody only recognizes one epitope of a single tumor antigen target, and even for the polyclonal antibody mixed by multiple monoclonal antibodies, the recognized epitope is limited and cannot cover complex epitopes of tumor cells. Many antibody screening technologies can also be used for screening polyclonal antibodies, but these technologies face a lot of challenges in the aspects of convenience of screening operation, the success rate of antibody screening, specificity of obtained antibodies and the like.

Therefore, an antibody library construction method needs to be developed for a technology for screening polyclonal antibodies against complex antigens, thereby solving the problems of complexity, diversity and mutability of tumor antigen and the limited available targets, and this method will have a wide application prospect and huge market value.

SUMMARY

In view of the deficiencies of the existing art and practical requirements, the present application provides an antibody library construction method and an application thereof. The method is designed based on the theory that a synNotch system controls the gene expression in cells. The extracellular recognition domain of the synNotch system is changed into an extracellular antibody library coding domain, and the regulated target gene is changed into a screening marker gene, so that an antigen-activated antibody screening system is obtained and a technology for screening polyclonal antibodies against complex antigens is obtained. In such a way, the problems of complexity, diversity and mutability of tumor antigen and the limited available targets are solved, and this method has a wide application prospect and huge market value.

To achieve this object, the present application adopts solutions below.

In a first aspect, the present application provides an antibody library construction method. The method is based on the principle that a synNotch system controls the gene expression in cells, and includes: inserting a first element and a second element into the same vector or different vectors, and transfecting the vector(s) to a cell to obtain an antibody expression cell library, i.e., the antibody library;

wherein the first element includes a CIS activator and a screening marker gene, and the second element includes an extracellular antibody library coding domain, a Notch core domain and an intracellular transcription domain.

The method specifically includes steps described below:
(1) transfecting a vector containing a CIS activator and a screening marker gene into a cell; and
(2) transfecting a vector carrying an extracellular antibody library coding domain, a Notch core domain and an intracellular transcription domain from an N terminus to a C terminus in sequence into the cell of the step (1) to obtain an antibody expression cell library, i.e., the antibody library.

The two vectors in the steps (1) and (2) may be integrated into one vector, and it is also feasible to construct the antibody library using this vector, while performing transfection in two steps with two vectors respectively can improve transfection efficiency and make it easier to construct a large-capacity antibody library. The vector includes an expression vector.

The present application is designed based on the principle that a synNotch system controls the gene expression in cells. The synNotch system includes the core regulatory domain of a natural intercellular signal transduction receptor Notch, and also includes a synthetic extracellular recognition domain and a synthetic intracellular transcription domain. The synthetic extracellular recognition domain is a single chain antibody. When the single chain antibody recognizes and binds to an antigen, the synNotch system undergoes the inducible transmembrane region shearing, thereby releasing the intracellular transcription domain into the cell nucleus, and the intracellular transcription domain binds to an upstream CIS activator to activate the expression of a regulated target gene. Therefore, cells modified by the synNotch system can drive the expression of a specific gene through specific antigen recognition and binding. When used for modifying T cells, the T cells can express cytokines under the regulation of antigens to kill target cells, or the T cells can express CAR under the regulation of antigens, thereby improving the recognition precision of the CAR-T cells to the target cells.

In the present application, in order to solve the defects of antibody screening in the existing art, the applicant provides a concise and effective antibody library construction method, with the theory that a synNotch system controls the gene expression in cells as a basic principle. Through a large number of experiments, the whole scheme flow process is optimized. Through repeated design and verification, the extracellular recognition domain of the synNotch system is changed into an extracellular antibody library coding domain, and the regulated target gene is changed into a screening marker gene, so that an antigen-activated antibody screening system is obtained. The antibody library construction method is to first transfect a vector containing a CIS activator and a screening marker gene into a cell and then transfect a vector carrying an extracellular antibody library coding domain, a Notch core domain and an intracellular transcription domain from an N terminus to a C terminus in sequence into the cell, to obtain an antibody expression cell library.

Preferably, the screening marker gene includes any one or a combination of at least two of a drug resistance gene, a suicide gene, a fluorescent protein gene, and a molecular tag.

If the positive screening for antibodies is to be performed, the screening marker gene is designed as a drug resistance gene such that the activated cells can survive in a medium with the screening drug and the rest cells die, thereby screening cells expressing an antibody against the target antigen. If the negative screening for antibodies is to be performed, the screening marker gene is designed as a suicide gene such that the activated cells become apoptotic in the medium with the screening drug and the rest cells survive, thereby removing cells expressing an antibody against the target antigen.

In the present application, the screening marker gene that can be used for performing the positive screening by using drugs can be, but is not limited to, a puromycin resistance gene, a neomycin resistance gene, a blasticidin resistance gene and a hygromycin B resistance gene, and the corresponding used drugs for screening are puromycin, G418, blasticidin and hygromycin B. The screening marker gene that can be used for performing the negative screening by using drugs can be, but is not limited to, a herpes simplex virus thymidine kinase (HSV-TK) gene, a cytosine deaminase (CD) gene and an iCasp9 suicide system gene, and the corresponding used drugs for screening are ganciclovir or FIAU, 5-fluorocytosine, AP1903 and AP20187.

Preferably, the drug resistance gene includes any one or a combination of at least two of a puromycin resistance gene, a neomycin resistance gene, a blasticidin resistance gene, and a hygromycin B resistance gene.

Preferably, the suicide gene includes any one or a combination of at least two of a herpes simplex virus thymidine kinase (HSV-TK) gene, a cytosine deaminase (CD) gene, and an iCasp9 suicide system gene.

Preferably, the fluorescent protein gene includes any one or a combination of at least two of EGFP, YFP, mCherry, DsRed, and BFP.

Preferably, the molecular tag includes any one or a combination of at least two of His-tag, Flag-tag, HA-tag, Myc-tag, and Strep-tag.

In the present application, the screening marker gene can be, but is not limited to, a fluorescent protein gene such as EGFP, YFP, mCherry, DsRed and BFP; and a molecular tag, i.e., a protein/polypeptide tag including but not limited to His-tag, Flag-tag, HA-tag, Myc-tag, and Strep-tag. Both the positive screening and the negative screening can be performed by detecting fluorescent or anti-tag antibodies through a flow cytometry.

A screening method for the screening marker gene includes any one or a combination of at least two of drug screening, flow cytometry detection and sorting, and magnetic-activated cell sorting.

Preferably, a screening drug for the drug resistance gene includes any one of puromycin, G418, blasticidin, and hygromycin B.

Preferably, a screening drug for the suicide gene includes any one or a combination of at least two of ganciclovir or FIAU, 5-fluorocytosine, AP1903, and AP20187.

Preferably, a detection and sorting method for the fluorescent protein gene includes flow cytometry detection and sorting.

Preferably, a detection and sorting method for the molecular tag includes flow cytometry detection and sorting.

Preferably, a detection and sorting method for the marker gene includes magnetic-activated cell sorting.

Preferably, the extracellular antibody library coding domain includes (an intact antibody, chains that make up an antibody or an antibody fragment) any one or a combination of at least two of an antibody sequence, an antibody heavy chain sequence, an antibody light chain sequence, an antibody variable region sequence, a single chain antibody sequence, a single domain antibody sequence, and a Fab fragment sequence.

In the present application, the extracellular antibody library coding domain portion includes, but is not limited to, an library composed of intact antibodies, chains that make up an antibody (heavy chains or light chains) or antibody fragments (antibody variable regions, single chain antibodies, single domain antibodies, or Fab fragments). The source of the extracellular antibody library coding domain can be, but is not limited to, prepared from an immunized animal, from a diseased human population, from a healthy human population, from a vaccinated human population, or artificially synthesized.

Preferably, the source of the extracellular antibody library coding domain includes any one or a combination of at least two of an immunized animal, a diseased human population, a healthy human population, a vaccinated human population, and artificial synthesis.

Preferably, the Notch core domain includes a human Notch, a mouse Notch, or a sequence having a similarity of not less than 85% to the human Notch or the mouse Notch.

Preferably, the Notch core domain includes P1391-R1763 fragment of a human, P1390-R1752 fragment of a mouse, fragments obtained by adding or deleting 200 amino acids or less at the front end or terminal end of these fragments, or sequences having a similarity of not less than 85% to these fragments.

Preferably, the human Notch has an amino acid sequence as shown in SEQ ID NO.1.

Preferably, the mouse Notch has an amino acid sequence as shown in SEQ ID NO.2.

In the present application, the Notch core domain may be from, but is not limited to, a human Notch, a mouse Notch, and a sequence having a similarity of not less than 85% to the human Notch or the mouse Notch. The Notch core domain may be the P1391-R1763 fragment (human), the P1390-R1752 fragment (mouse), fragments obtained by adding or deleting 200 amino acids or less at the front end or terminal end of these fragments, or sequences having a similarity of not less than 85% to these fragments.

Preferably, the intracellular transcription domain includes, but is not limited to, tTA and/or Gal4-VP64.

Preferably, the CIS activator includes pTet and/or UAS-pSV40.

Preferably, the transcription domain includes tTA and/or Gal4-VP64.

Preferably, a method for transfecting includes any one or a combination of at least two of viral transfection, transfection with a chemical transfection reagent, and electroporation transfection.

Preferably, the coding domain, the domain or the gene contains any one or a combination of at least two of an amino acid sequence encoding a protein, a DNA sequence encoding a protein, and an RNA sequence encoding a protein.

In a second aspect, the present application provides an antibody library. The antibody library is constructed according to the method described in the first aspect.

In a third aspect, the present application provides a method for screening antibodies. The method uses the antibody library described in the second aspect to perform screening and includes the following steps:
(1) contacting the antibody library with an antigen; and
(2) screening a cell expressing a target antibody according to expression of the screening marker gene;

wherein the antibody includes a monoclonal antibody or a polyclonal antibody;

the antigen includes any one or a combination of at least two of a wild cell, a cell transfected with a specific antigen gene, a cell bound to a specific antigen, an antigen dissolved in a culture medium, an antigen coated on a culture vessel, an antigen coated on a microsphere, and an antigen coated on a culture scaffold.

In the present application, the method for screening antibodies is to contact an antibody expression cell library with an antigen. Only antibody expression cell capable of recognizing the antigen can activate the expression of the screening marker gene in the cell, so that a cell expressing a target antibody is screened according to the expression of the screening marker gene.

In a fourth aspect, the present application provides an antibody. The antibody is obtained by screening according to the method described in the third aspect.

In another aspect, the present invention further provides a system for screening antibodies. The system includes:
a first element including a CIS activator and a screening marker gene; and
a second element including a gene for encoding an extracellular antibody library coding domain, a gene for encoding a Notch core domain and a gene for encoding an intracellular transcription domain.

The CIS activator, the screening marker gene, the extracellular antibody library coding domain, the Notch core domain and the intracellular transcription domain are defined as described above.

In another aspect, the present invention further provides a method for screening antibodies using the above system. The method includes the following steps:
transfecting a first element and a second element into a cell, where the first element includes a CIS activator and a screening marker gene, and the second element includes a gene for encoding an extracellular antibody library coding domain, a gene for encoding a Notch core domain and a gene for encoding an intracellular transcription domain;
allowing the cell to express the extracellular antibody library coding domain;
contacting the cell with an antigen; and
screening a cell expressing a target antibody according to expression of the screening marker gene to screen the target antibody.

The CIS activator, the screening marker gene, the extracellular antibody library coding domain, the Notch core domain and the intracellular transcription domain are defined as described above.

Compared with the existing art, the present application has beneficial effects described below.

1. The method provided in the present application can screen both monoclonal antibodies and polyclonal antibodies. The conventional antibody screening technology is only suitable for screening monoclonal antibodies, and even if it is used for screening polyclonal antibodies, the diversity, specificity and stability of the screened antibodies are difficult to ensure. The polyclonal antibodies screened against the antigen by using the antibody screening technology provided in the present application have a greater diversity. Antibodies with better specificity and higher affinity can be obtained by changing screening conditions. The coding sequences of a large number of monoclonal antibodies can be obtained through sequencing. The antibody screening technology provided herein is simpler than the conventional monoclonal screening technology.

2. The method provided in the present application does not need to express and purify antigens. When the prior antibody screening technology is used to perform antibody screening, the antigen proteins or the peptide segments of antigen epitopes need to be expressed and purified for immunizing animals, plating for ELISA antibody screening and binding to antibodies to screen antibodies through a flow cytometry. However, for the conventional antibody screening technology, some of the antigen proteins or the peptide segments are not easy to purify, or are modified differently from the original antigen proteins or do not have the original spatial structure, which affects the specificity and the affinity of the screened antibodies. With the antibody screening technology provided in the present application, the antibody screening can be performed readily by displaying the target antigen on the surface of the cell. The cell displaying the target antigen can be obtained readily by transfecting the gene of the target antigen into the cell. Alternatively, a wild cell that is identified to express the target antigen may be directly used. The antibody screening technology provided herein is very convenient.

3. The method provided in the present application does not need to preset antigens. The conventional antibody screening technology needs to identified antigens in advance and then screens antibodies against the antigens. However, tumor cells are extremely complex, there are a large amount of un-identified antigens, and the identified tumor antigen targets are very limited, so the antibodies screened against the limited antigen targets cannot meet the requirements of tumor treatment. The method provided in the present application does not need to preset antigens, and instead, can take the whole tumor cell as the antigen, and screen polyclonal antibodies that can recognize various antigen targets on the surface of the tumor cell from the antibody library, thereby avoiding the problem that the known antigen targets are limited.

4. The method provided by the present application can conveniently perform negative screening. The purpose of the negative antibody screening is to remove undesired antibodies, such as antibodies that may recognize normal cells. Since tumor cells and normal cells have a large amount of identical antigens, the antibodies screened against tumor cells may also recognize normal cells besides tumor cells, thereby causing the developed antibody drugs to have side effects of damaging normal tissues. When the conventional antibody screening technology is used to screen monoclonal antibodies, the effect of the screened antibodies on normal cells can be verified one at a time so as to remove undesired antibodies. Such method is inefficient and is not suitable for screening polyclonal antibodies. The antibody screening technology provided in the present application can conveniently perform negative screening by using a negative screening marker gene in a manner of using a negative screening drug or negatively sorting with a flow cytometer.

5. The method provided in the present application has various screening modes. The antibody screening technology provided herein can perform both positive and negative screening by using drugs, may also perform screening by using a flow cytometer, and may also perform screening in a mode combining the drug screening and the flow cytometer screening. The screening mode can be freely selected and matched according to research conditions and research experiences, which is more favorable for obtaining the target antibody.

DETAILED DESCRIPTION

To further elaborate on the technical means adopted and the effects achieved in the present application, the solutions of the present application are further described below through specific examples in conjunction with drawings, but the present application is not limited to the scope of the examples.

Example 1 Screening of Known CD19 and GPC3 Antibodies

Figure 1:
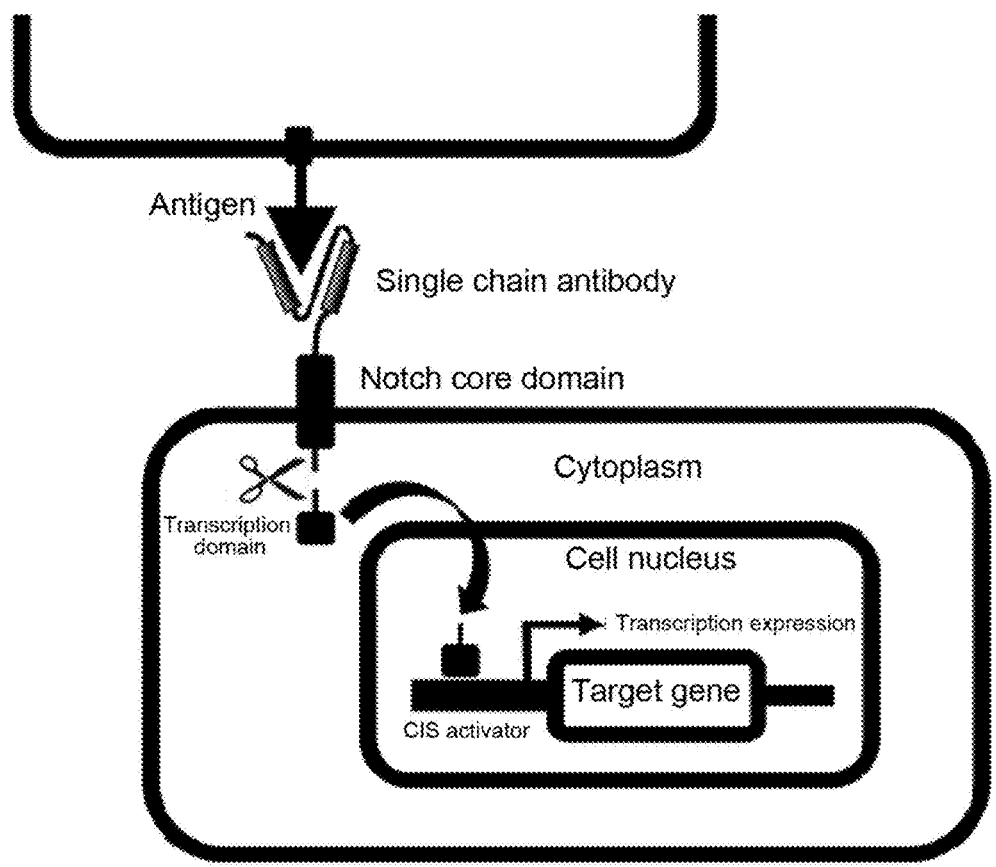
FIG. 1 is a schematic diagram showing a principle that a synNotch system controls the gene expression in cells according to the present application.

FIG. 1 shows a principle that a synNotch system controls the gene expression in cells. When the extracellular single chain antibody of the synNotch system recognizes and binds to an antigen, the synNotch system undergoes the inducible transmembrane region shearing, thereby releasing the intracellular transcription domain into the cell nucleus, and the intracellular transcription domain binds to the upstream CIS activator to activate the expression of a regulated target gene.

Figure 2:
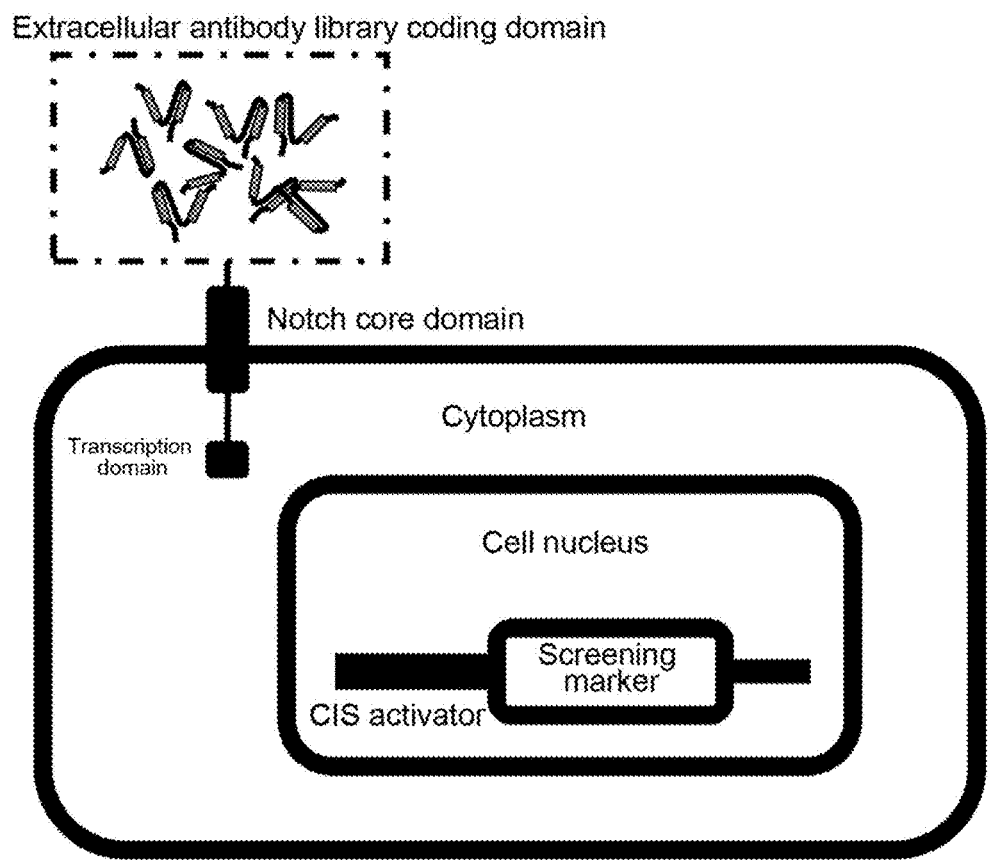
FIG. 2 shows a synNotch-based antibody screening system according to the present application.

The principle of a synNotch-based antibody screening system is shown in FIG. 2. Based on the synNotch system, the extracellular recognition domain is changed into an extracellular antibody library coding domain, and the regulated target gene is changed into a screening marker gene, so that an antigen-activated antibody screening system is obtained.

Antibodies specific for CD19 and GPC3 were screened from a known mixed antibody library of CD19 and GPC3, respectively.

Figure 3:
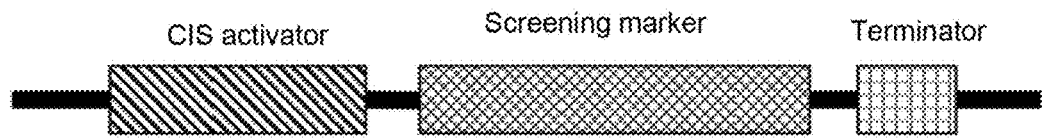
FIG. 3 is a schematic diagram showing a vector containing a CIS activator and a screening marker gene according to the present application.

(1) Construction of a Monoclonal Cell Line Stably Transfected with the CIS Activator and the Screening Marker Gene In this example, pTet (SEQ ID NO.3) was used as the CIS activator. The pTet initiated the expression of the screening gene after receiving a tTA signal. A fluorescent protein fused with a puromycin resistance gene (SEQ ID NO.4) was used as the screening marker, and the fluorescent protein and the puromycin resistance gene was linked by a 2A (SEQ ID NO.5) sequence that could be automatically broken. The vector containing the CIS activator and the screening marker gene is schematically shown in FIG. 3.

Figure 4:
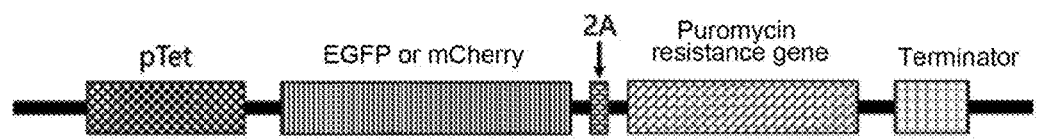
FIG. 4 is a schematic diagram showing a vector containing a fluorescent protein fused with a puromycin resistance gene under the regulation of a CIS activator pTet according to the present application.

In this example, two fluorescent proteins, i.e., EGFP (SEQ ID NO.6) and mCherry (SEQ ID NO.7), were used to fuse with the puromycin resistance gene to construct two screening markers, respectively. SV40 polyplex A (SEQ ID NO.8) was used as the terminator. The coding genes of entire sequences (FIG. 4) were directly artificially synthesized, and then constructed into a lentiviral vector, packaged into lentivirus, and then transfected into 293T cells, respectively. 3 days later, the transfected cells were monoclonalized.

Figure 5:
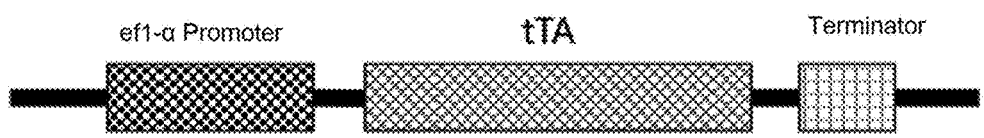
FIG. 5 is a schematic diagram showing a tTA expression vector according to the present application.

To screen the monoclonal cell line to obtain correct monoclonal cells, a tTA expression vector (FIG. 5) needed to be constructed. The tTA expression vector consisted of an ef1-α promoter (SEQ ID NO.9), a tTA gene (SEQ ID NO.10) and a terminator. The tTA expression vector was constructed into a lentiviral vector and packaged into a lentivirus.

Figure 6:
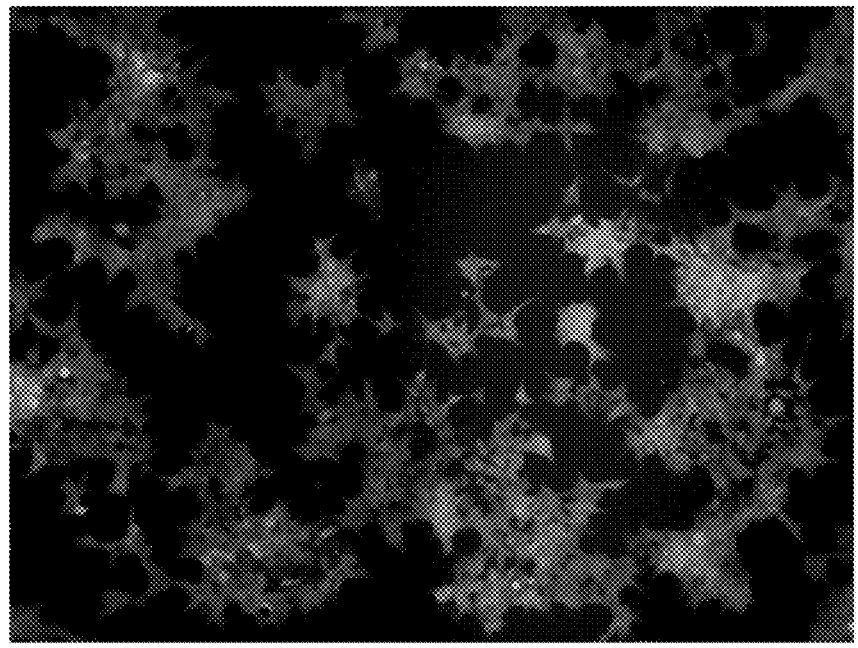
FIG. 6 is a diagram indicating that tTA activates a CIS activator pTet to express a green fluorescent protein, as shot by a fluorescence microscope according to the present application.
Figure 7:
FIG. 7 is a diagram indicating that tTA activates a CIS activator pTet to express a red fluorescent protein, as shot by a fluorescence microscope according to the present application.

A portion of cells was got from monoclonal cells to be screened and then transfected with the tTA expression lentivirus. 2-3 days later, the cells were observed by a fluorescence microscope. Cell lines that expressed EGFP (FIG. 6, observed under the microscope for green fluorescent expression when monoclonal cells stably transfected with the green fluorescent protein fused with the puromycin resistance gene under the regulation of the CIS activator pTet) or mCherry (FIG. 7, observed under the microscope for red fluorescent expression when monoclonal cells stably transfected with the red fluorescent protein fused with the puromycin resistance gene under the regulation of the pTet CIS activator were screened), but had no fluorescent expression before transfection, were monoclonal cell lines that had been stably transfected with the pTet CIS activator and the screening marker gene.

Figure 8:
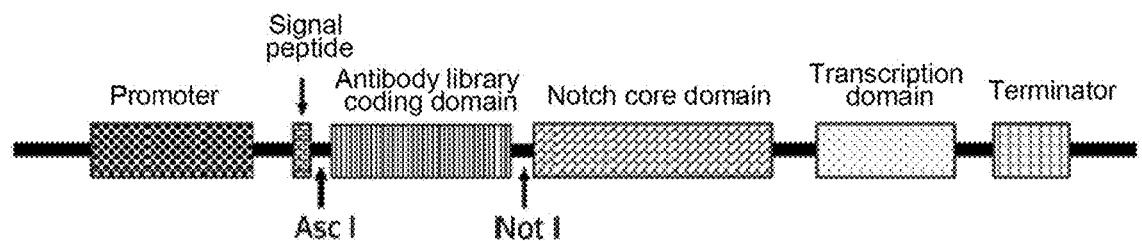
FIG. 8 is a schematic diagram showing a universal expression vector of an antibody library according to the present application.

(2) Construction of an antibody expression cell library: First, an intermediate vector including all components in the antibody gene library expression vector, other than the extracellular antibody library coding domain gene, was constructed to facilitate the subsequent insertion of the extracellular antibody library coding domain gene (FIG. 8, a schematic diagram showing a universal expression vector of an antibody library). Sequences of each component of the intermediate vector were synthesized. From the N terminus to C terminus, the components of the vector in series were an mPGK1 promoter (SEQ ID NO.11), a CD8α signal peptide (SEQ ID NO.12) coding sequence, an antibody gene library coding domain (a coding region sequence with a β-galactosidase (lacZ) N-terminus α fragment which was behind an Asc I restriction endonuclease site and was in front of a Not I restriction endonuclease site, for facilitating insertion of antibody library sequences and for displaying fragment insertion through blue-white spots), a NOTCH1 fragment (P1390-R1752 fragments containing a transmembrane region in SEQ ID NO.2) coding sequence, a tTA coding sequence, and a terminator. The synthesized sequences were constructed into a lentiviral vector for further insertion of the antibody gene sequence.

Figure 9:
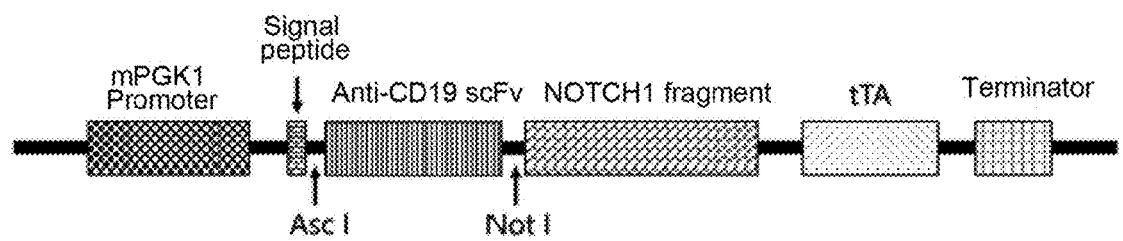
FIG. 9 is a schematic diagram showing an expression vector of an anti-CD19 single chain antibody according to the present application.

The coding sequences of the known anti-human CD19 single chain antibody (SEQ ID NO.13) and anti-human GPC3 single chain antibody (SEQ ID NO.14) with Asc I and Not I restriction endonuclease sites at both terminuses were synthesized and inserted between the Asc I and Not I restriction endonuclease sites of the intermediate vector, respectively. The vector inserted with the anti-human CD19 single chain antibody gene (FIG. 9) was packaged into a lentivirus and transfected into a monoclonal cell line with the EGFP screening marker to yield CD19 single chain antibody expression cells.

Figure 10:
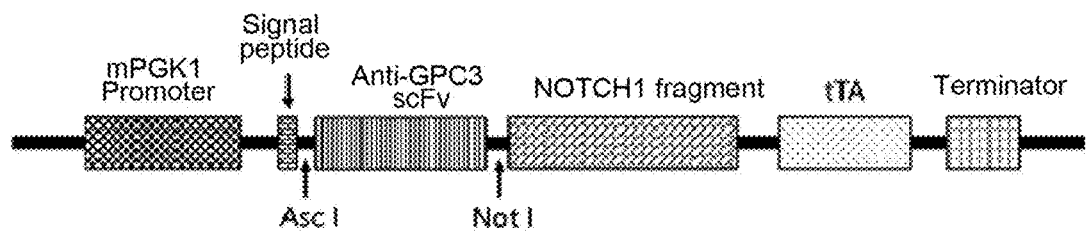
FIG. 10 is a schematic diagram showing an expression vector of an anti-GPC3 single chain antibody according to the present application.

The vector inserted with the anti-human GPC3 single chain antibody gene (FIG. 10) was packaged into a lentivirus and transfected into a monoclonal cell line with the mCherry screening marker to yield GPC3 single chain antibody expression cells.

Figure 11:
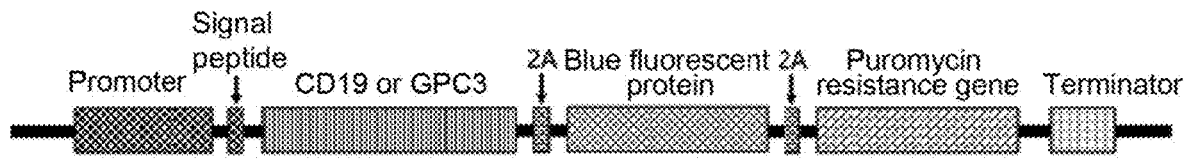
FIG. 11 is a schematic diagram showing an expression vector of a CD19 or GFPC3 antigen according to the present application.

(3) Construction of CD19 and GFPC3 antigen expression cells: The coding sequences of CD19 (SEQ ID NO.15) and GPC3 (SEQ ID NO.16) antigens were synthesized and constructed into expression vectors respectively. In the expression vector, CD19 or GPC3, a blue fluorescent protein (SEQ ID NO.17), and a puromycin resistance gene were fused through two 2A sequences (FIG. 11).

Figure 12:
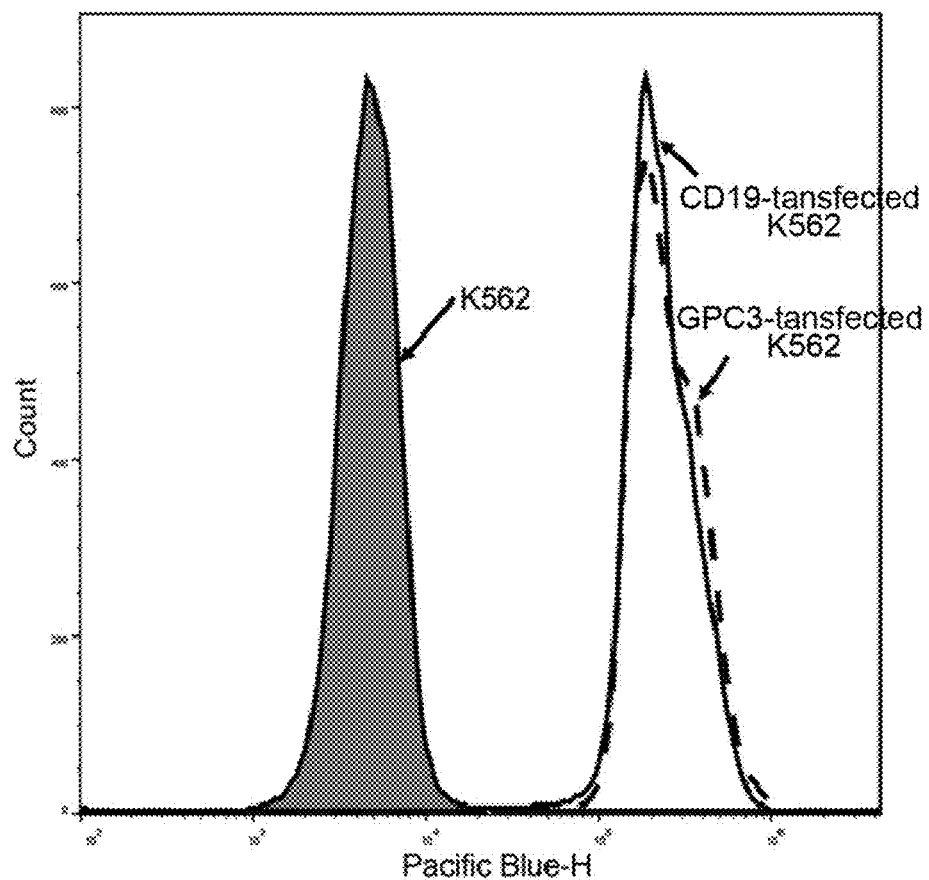
FIG. 12 is a diagram showing expression of the CD19 and GFPC3 antigens in K562 cells, as detected through a flow cytometry according to the present application.

The constructed expression vector was packaged into a lentivirus and transfected into K562 cells through virus. After 2 days of transfection, K562 cells expressing CD19 or GPC3 stably were screened by adding 1 μg/mL purinomycin into the culture medium. The expression of the blue fluorescent protein detected by the flow cytometry almost reached 100% (FIG. 12), indicating that the antigen had been stably expressed in K562 cells.

Figure 13:
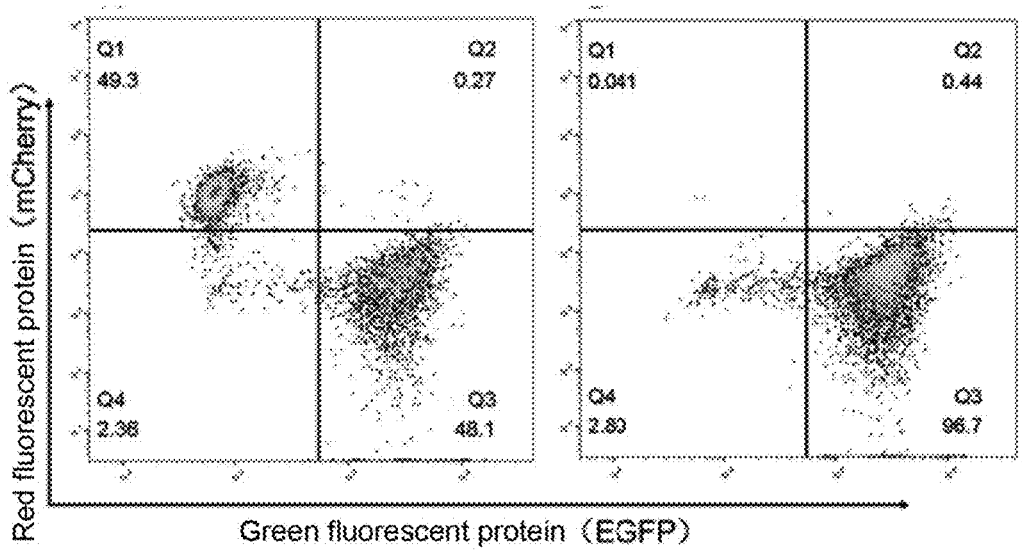
FIG. 13 is a graph showing results of screening CD19 antibody expression cells from a mixed antibody expression cell library by using the antibody screening system according to the present application.

(4) Screening of CD19 antibody expression cells from the mixed antibody expression cell library: CD19 single chain antibody expression cells and GPC3 single chain antibody expression cells were mixed in a ratio of 1:1. The mixed cells were mixed with CD19 antigen expression cells in a ratio of 1:1. After the mixed cells were cultured for 2 days, 1 μg/mL puromycin was added to the culture medium for screening. After 8-10 days of screening, the antibody expression cells were almost cells with green fluorescence expressing the CD19 antibody (FIG. 13). When cells expressing both the CD19 single chain antibody and green fluorescence were mixed with cells expressing both the GPC3 single chain antibody and red fluorescence in a ratio of 1:1, and screened by mixing with CD19 antigen expression cells and adding puromycin, almost all of the cells obtained were cells expressing the CD19 antibody with green fluorescence.

Figure 14:
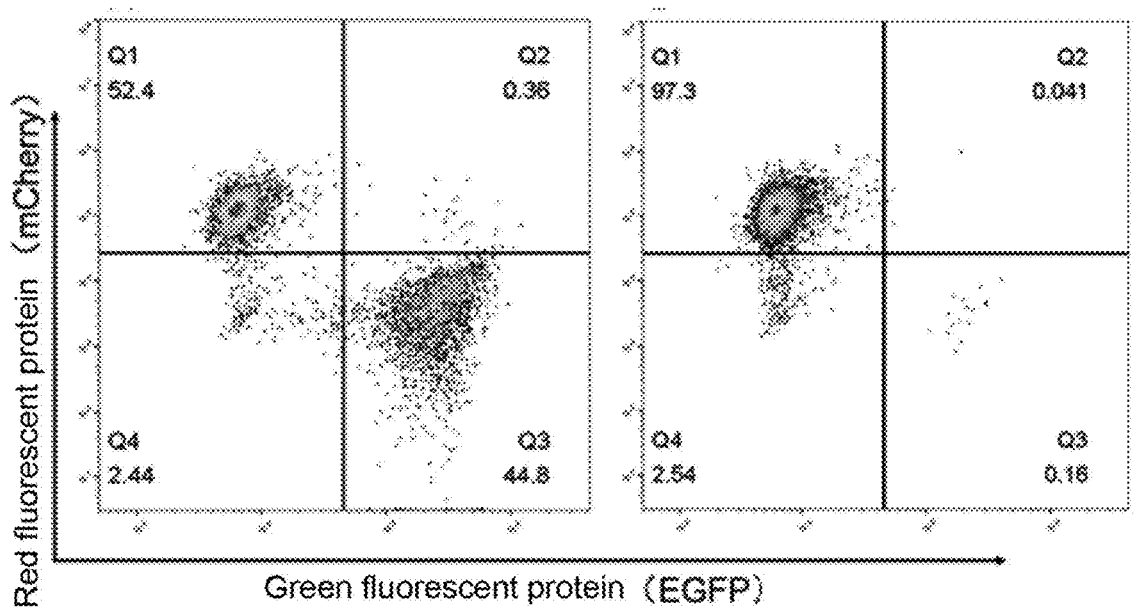
FIG. 14 is a graph showing results of screening GPC3 antibody expression cells from a mixed antibody expression cell library by using the antibody screening system according to the present application.

(5) Screening of cells expressing the anti-GPC3 antibody from the mixed cells: CD19 antibody expression cells and GPC3 antibody expression cells were mixed in a ratio of 1:1. The mixed cells were mixed with GPC3 antigen expression cells in a ratio of 1:1. After the mixed cells were cultured for 2 days, 1 μg/mL of puromycin was added to the culture medium for screening. After 8-10 days of screening, the antibody expression cells were almost cells with red fluorescence expressing the GPC3 antibody (FIG. 14). When cells expressing both the CD19 single chain antibody and green fluorescence were mixed with cells expressing both the GPC3 single chain antibody and red fluorescence in a ratio of 1:1, and screened by mixing with GPC3 antigen expression cells and adding puromycin, almost all of the cells obtained were cells expressing the GPC3 antibody with red fluorescence.

These results of the above experiment indicate that a single chain antibody against a target antigen can be screened from a known antibody library according to this antibody screening method.

Figure 15:
FIG. 15 is a schematic diagram showing a vector containing a green fluorescent protein under the regulation of a CIS activator pTet according to the present application.

Example 2 Preparation of the Antibody Library and Screening of CD19 Antibody Expression Cells Through the Flow Cytometry (1) Construction of a Monoclonal Cell Line Stably Transfected with the CIS Activator and the Screening Marker Gene In this example, the CIS activator pTet was used. The pTet initiated the expression of the screening marker green fluorescent protein gene after receiving a tTA signal. An entire sequence (FIG. 15) was artificially synthesized and constructed into a lentiviral vector. Lentivirus was packaged and then transfected into 293T cells. 3 days later, the transfected cells were monoclonalized. A portion of cells was got from monoclonal cells to be screened and then transfected with lentivirus expressing tTA. 2-3 days later, the cells were observed through a fluorescence microscope. A cell line with green fluorescent expression, which had no fluorescent expression before transfection, was selected as the monoclonal cell line stably transfected with the CIS activator and the screening marker gene.

(2) Construction of an Antibody Expression Cell Library

C57BL/6J mice were immunized with CD19-positive Raji cells. The booster immunization was performed once two weeks later and once at the fourth week. The mice were sacrificed three days later. Splenic lymphocytes of the mice were isolated. RNA was extracted from splenic lymphocytes by using an RNA extraction purification kit.

Figure 16:
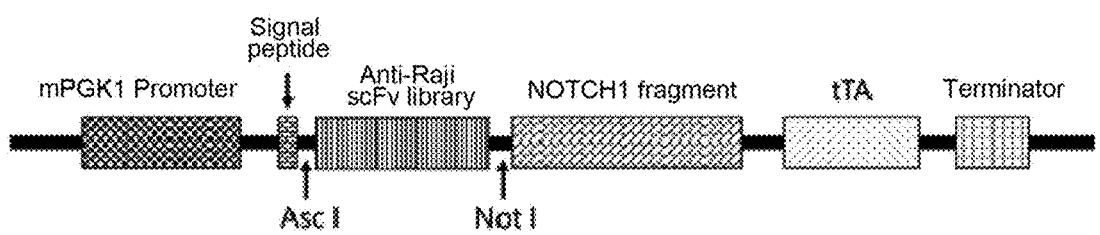
FIG. 16 is a schematic diagram showing an anti-Raji single chain antibody gene library expression vector according to the present application.

Reverse transcription was performed on the extracted RNA by using a reverse transcription primer of a light chain (SEQ ID NO.18) and a reverse transcription primer of a heavy chain (SEQ ID NO.19) with a reverse transcription kit, respectively. The heavy and light chains were amplified with degenerate primers, respectively. Then the light and heavy chains were linked by overlapping PCR to form a light chain-linker-heavy chain scFv library. DNA fragments of the scFv library were digested by both Asc I and Not I and then were inserted between the Asc I and Not I restriction endonuclease sites of the intermediate vector of the antibody gene library expression vector to yield the antibody gene library expression vector (FIG. 16). Single chain antibodies prepared from Raji cell-immunized mice were cloned into the antibody gene library expression vector.

The antibody gene library expression vector was packaged into a lentivirus and transfected into the monoclonal cell line stably transfected with the CIS activator and the screening marker gene obtained in the step (1), to obtain the antibody expression cell library.

(3) Construction of Antigen Expression Cells

Figure 17:
FIG. 17 is a schematic diagram showing an antigen expression vector used for negative screening according to the present application.

The preparation of the antigen expression cells expressing CD19 was referred to Example 1. This antigen expression cell was used for positive screening of anti-CD19 antibodies. A coding gene of a transmembrane domain (SEQ ID NO.20) was synthesized and was used to replace the CD19 antigen gene in the positive screening vector to obtain an antigen expression vector for negative screening (FIG. 17).

Figure 18:
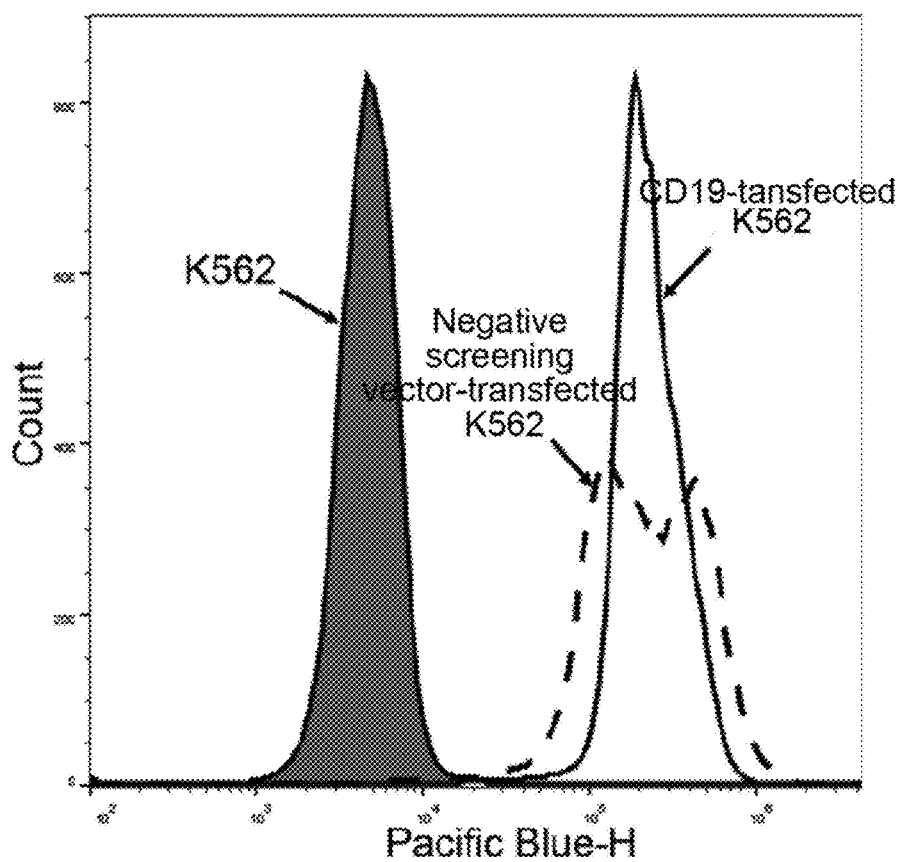
FIG. 18 is a graph showing results of expression of the CD19 antigen expression vector and the antigen expression vector used for negative screening in K562 cells, as detected by a flow cytometry according to the present application.

The constructed antigen expression vectors were packaged into lentiviruses respectively and transfected into K562 cells through viruses. After 2 days of transfection, a positive screening antigen expression cell line and a negative screening antigen expression cell line were screened by adding 1 μg/mL purinomycin into the culture medium. The expression of the blue fluorescent protein detected through the flow cytometry almost reached 100% (FIG. 18), indicating that the antigen had been stably expressed in K562 cells.

(4) Screening of Cells Expressing the CD19 Antibody Through the Flow Cytometry

Figure 19:
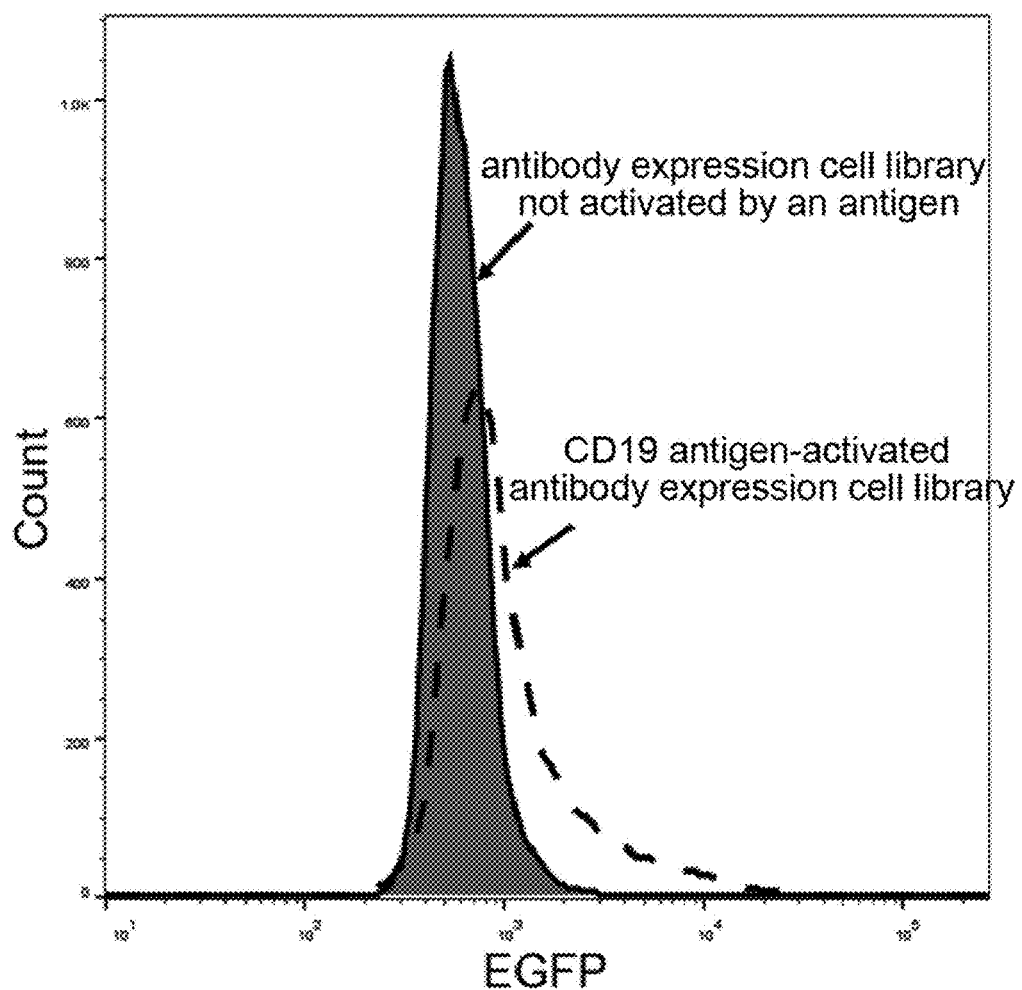
FIG. 19 is a graph showing induction and activation of an antibody expression cell library before screening, as detected through a flow cytometry according to the present application.

The antibody expression cell library was mixed with the positive-screening cells expressing the CD19 antigen in a ratio of 1:1. After the mixed cells were cultured for 2 days, a small number of cells expressing the green fluorescent protein appeared in the antibody expression cell library (FIG. 19). After the antibody expression cell library and the positive-screening cells expressing the CD19 antigen were mixed and then cultured for 2 days, a small number of cells expressing the green fluorescent protein appeared in the antibody expression cell library. The cells expressing the green fluorescent protein were sorted through a sorting flow cytometry and continued to be cultured until most of the green fluorescence disappeared.

Figure 20:
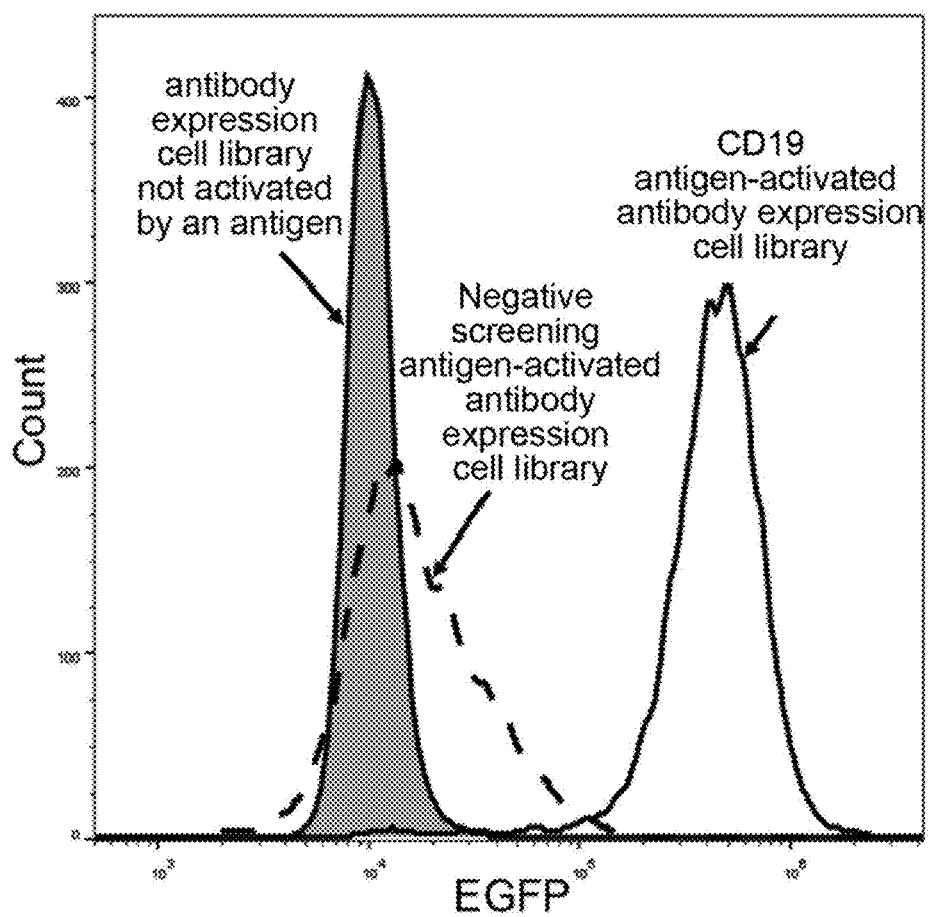
FIG. 20 is a graph showing induction and activation of an antibody expression cell library after screening, as detected through a flow cytometry according to the present application.

The sorted antibody expression cell library was mixed with the negative-screening antigen expression cells in a ratio of 1:1. 3 days later, cells that were negative to both the green fluorescent protein and the blue fluorescent protein were sorted through the sorting flow cytometry, i.e., cells expressing the CD19 antibody. The antibody expression cells thus obtained, when co-cultured with the negative-screening antigen expression cells, expressed no green fluorescent protein, and, when co-cultured with the CD19 antigen expression cells, expressed the green fluorescent protein (FIG. 20). The antibody expression cells obtained after the positive-negative screening, when co-cultured with the negative-screening antigen expression cells, expressed no green fluorescent protein, and, when co-cultured with the CD19 antigen expression cells, expressed the green fluorescent protein.

Example 3 Preparation of the Antibody Library and Screening of CD19 Antibody Expression Cells Using Drugs (1) Construction of a Monoclonal Cell Line Stably Transfected with the CIS Activator and the Screening Marker Gene In this example, pTet was used as the CIS activator. An iCasp9 negative screening system (SEQ ID NO.21), a green fluorescent protein and a puromycin resistance gene were used as a screening marker, in which the iCasp9 negative screening system, the green fluorescent protein and the puromycin resistance gene were linked by 2A sequences that could be automatically broken.

Figure 21:
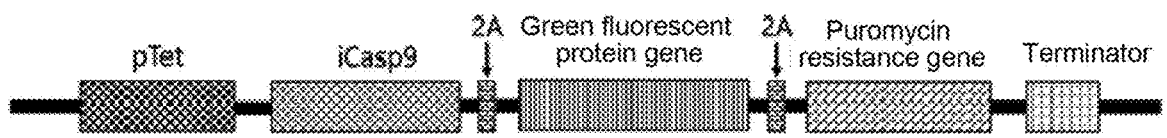
FIG. 21 is a schematic diagram illustrating a vector containing a fluorescent protein fused with a positive/negative screening gene under the regulation of a CIS activator pTet according to the present application.

An entire sequence (FIG. 21) was artificially synthesized, constructed into a lentiviral vector, packaged into lentivirus and then transfected into 293T cells. 3 days later, the transfected cells were monoclonalized. A portion of cells was got from monoclonal cells to be screened and then transfected with the lentivirus expressing tTA in Example 1. 2-3 days later, the cells were observed through a fluorescence microscope. A cell line with green fluorescent expression, which had no fluorescent expression before transfection, was selected as the monoclonal cell line stably transfected with the CIS activator and the screening marker gene.

(2) Construction of an Antibody Expression Cell Library

Figure 22:
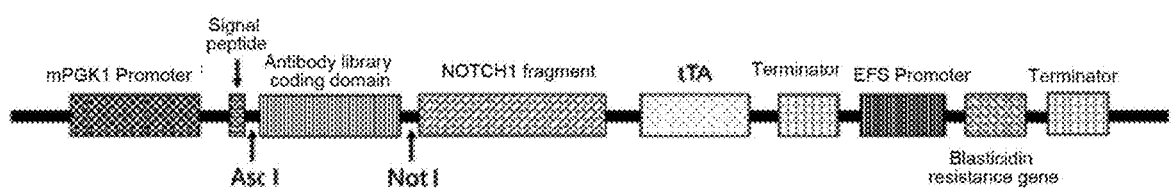
FIG. 22 is a schematic diagram showing a single chain antibody gene library expression vector for primary drug screening according to the present application.

First, an intermediate vector including all components in the antibody gene library expression vector, other than the extracellular antibody library coding domain gene, was constructed to facilitate the subsequent insertion of the extracellular antibody library coding domain gene (FIG. 22). Sequences of each component of the intermediate vector were synthesized. From the N terminus to C terminus, the components of the vector in series were an mPGK1 promoter, a CD8α signal peptide coding sequence, an antibody gene library coding domain (a coding region sequence with a β-galactosidase (lacZ) N-terminus α fragment which was behind an Asc I restriction endonuclease site and was in front of a Not I restriction endonuclease site, for facilitating insertion of antibody library sequences and for displaying fragment insertion through blue-white spots), a NOTCH1 fragment coding sequence, a tTA coding sequence, a terminator, an EFS promoter (SEQ ID NO.22), a blasticidin resistance (SEQ ID NO.23) gene, and a terminator.

The synthesized sequences were constructed into a lentiviral vector for further insertion of the antibody gene library sequence. DNA fragments of the scFv library of the Raji-immunized mice were digested by both Asc I and Not I and then were inserted between the Asc I and Not I restriction endonuclease sites of the intermediate vector of the antibody gene library expression vector to yield the antibody gene library expression vector. The antibody gene library expression vector was packaged into a lentivirus and then transfected to the monoclonal cell line stably transfected with the CIS activator and the screening marker gene. 2 days later, 10 m/mL blasticidin was added to the culture medium for primary screening to obtain the antibody expression cell library.

(3) Screening of Cells Expressing the CD19 Antibody Using Drugs

Figure 23:
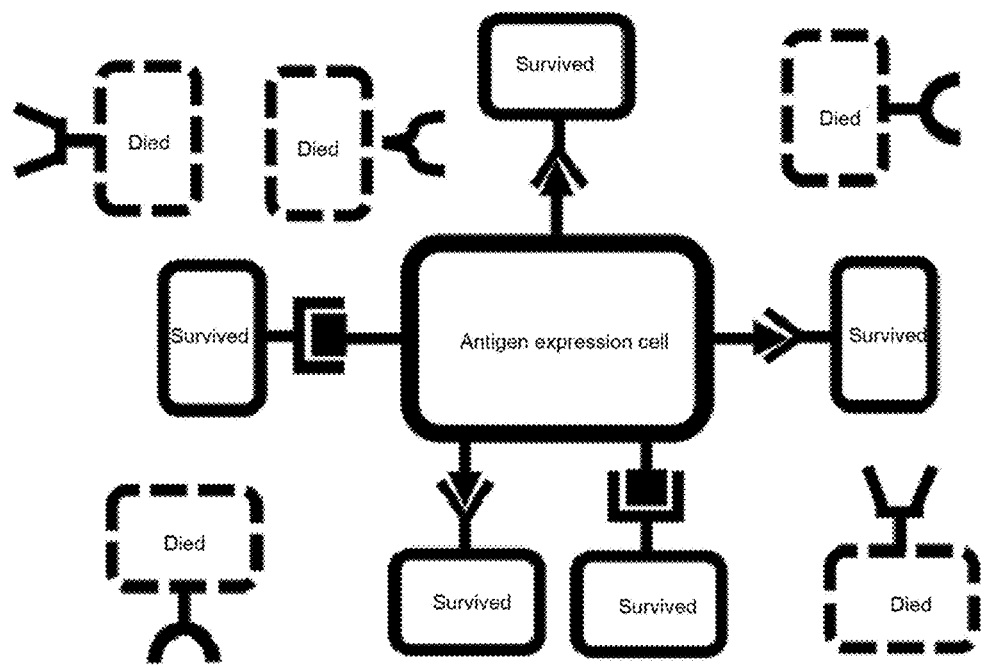
FIG. 23 is a schematic diagram showing a principle of drug positive screening by using an antibody screening system according to the present application.
Figure 24:
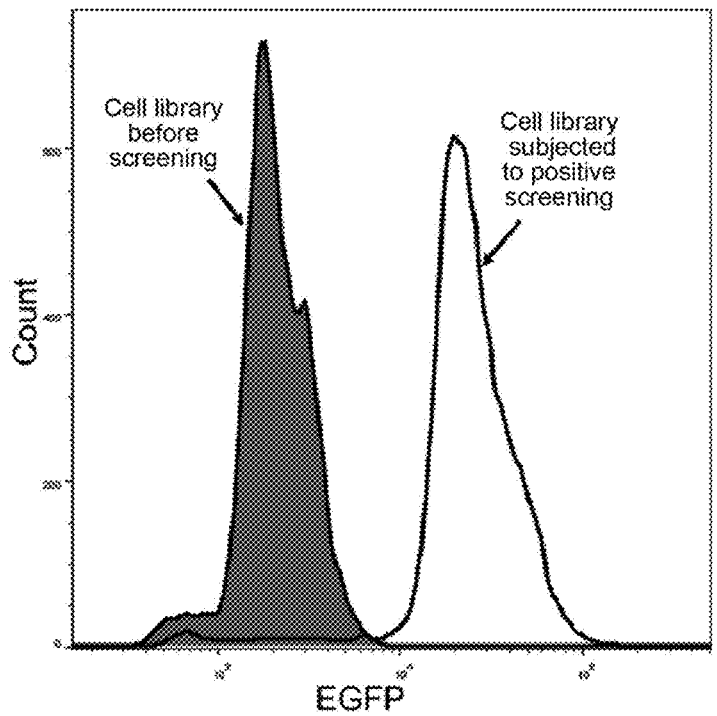
FIG. 24 is a graph showing results of positively screening of antibody expression cells, as detected through a flow cytometry according to the present application.

The antibody expression cell library and positive-screening cells expressing the CD19 antigen were mixed in a ratio of 1:1. After the mixed cells were cultured for 2 days, 1 µg/mL puromycin was added to the culture medium for screening. After 6-8 days of positive screening (the principle of positive screening was shown in FIG. 23), almost all of the antibody library expression cells were cells expressing the green fluorescence protein (FIG. 24). When the mixed antibody library expression cells and positive-screening cells expressing the CD19 antigen were subjected to positive screening through puromycin, almost all of the antibody expression cells were cells expressing the green fluorescence protein.

Figure 25:
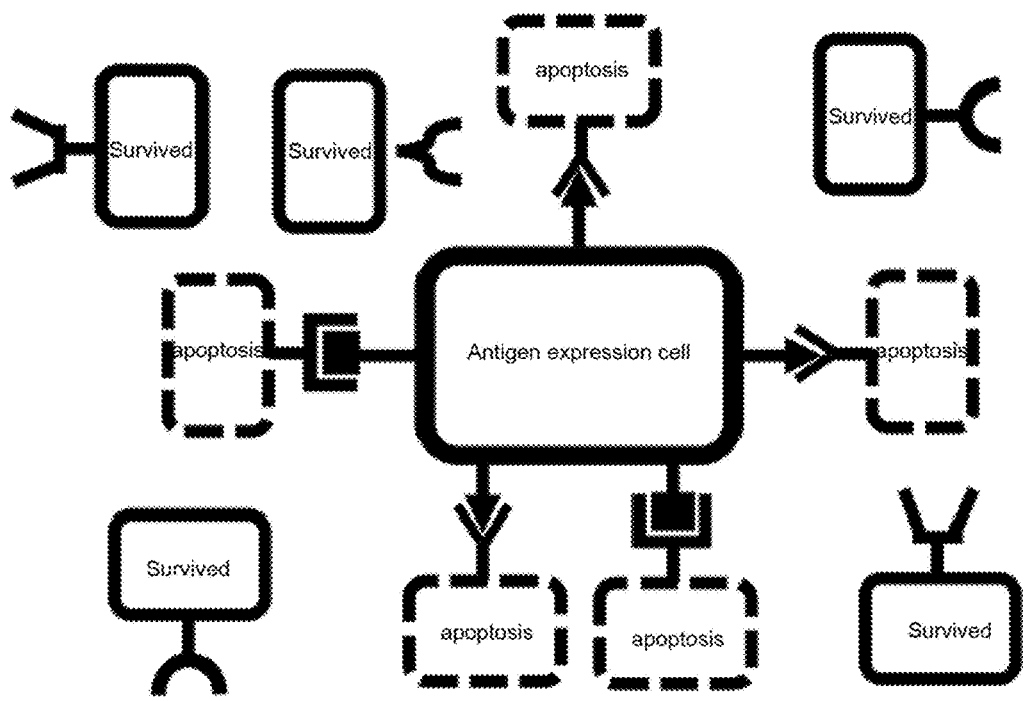
FIG. 25 is a schematic diagram showing a principle of drug negative screening by using an antibody screening system according to the present application.
Figure 26:
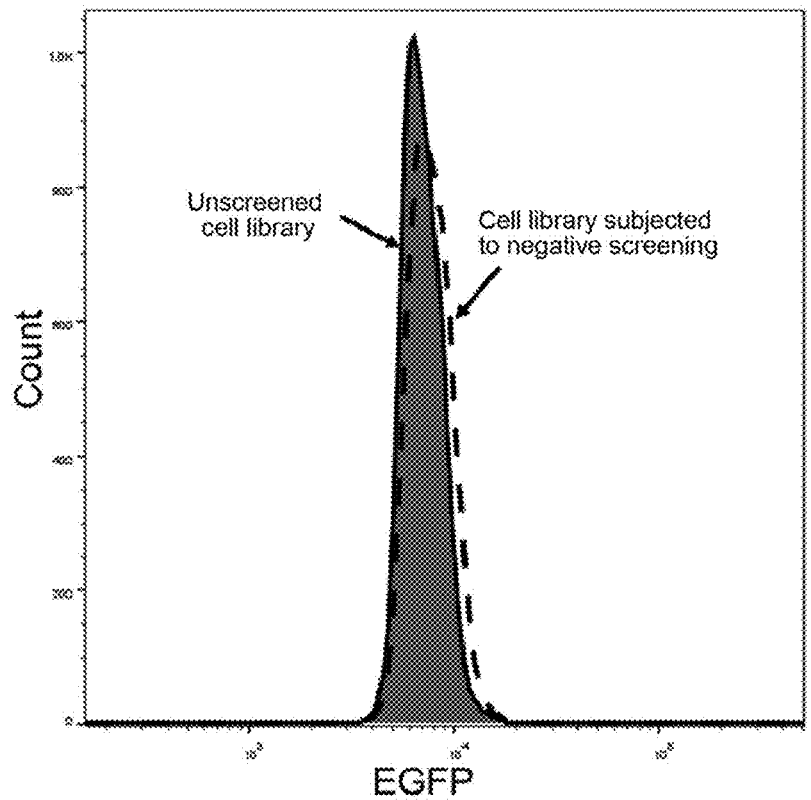
FIG. 26 is a graph showing results of negatively screening of antibody expression cells, as detected through a flow cytometry according to the present application.

10 µg/mL blasticidin was added to the culture medium of the mixed cells until blue fluorescent positive-screening antigen cells completely disappeared. The antibody library expression cells subjected to positive screening were continued to be cultured until the green fluorescent protein was almost not expressed. Then the antibody library expression cells and negative-screening antigen expression cells were mixed in a ratio of 1:1. 10 nM of AP1903 was added to the culture medium for negative screening (the principle of negative screening was shown in FIG. 25) until the green fluorescent protein was not expressed in the cultured antibody expression cells (FIG. 26). When the mixed antibody library expression cells and negative-screening cells were subjected to AP1903 negative selection, almost all of the antibody expression cells were cells that did not express green fluorescent protein.

Finally, 10 µg/mL blasticidin was added to the culture medium of the mixed cells until blue fluorescent negative-screening antigen cells completely disappeared. In this case, the antibody library expression cells were cells expressing the CD19 antibody.

Figure 27:
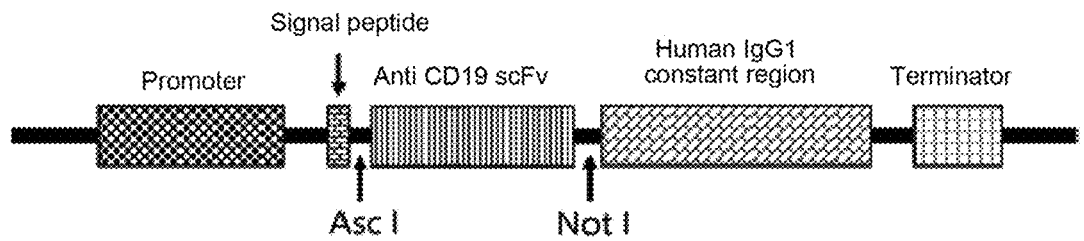
FIG. 27 is a schematic diagram showing an expression vector of a single chain antibody fused with an antibody constant region according to the present application.

Example 4 Characterization of Antibody Binding (1) Cloning of Antibody Coding Sequences of Screened CD19 Antibody Expression Cells Genomes of the screened CD19 antibody expression cells were extracted by using the DNeasy Blood & Tissue Kit (manufactured by Qiagen) according to the instructions of the kit. With the extracted genomes as a template, the coding gene of scFv was amplified by using a primer pair (SEQ ID NO.24, SEQ ID NO.25). The amplified product was digested by both Asc I and Not I, then inserted into an expression vector digested by both Asc I and Not I, and fused with an IgG1 constant region (SEQ ID NO.26) of the human (FIG. 27).

The linked vector was transfected into competent cells. The competent cells were coated on a petri dish containing an LB solid medium with 100 mg/L ampicillin. In the next day, about 20 clones were picked out from the petri dish, then inoculated in an LB liquid medium containing 100 mg/L ampicillin respectively and cultured in shaking flasks. The remaining colonies on the petri dish were eluted with the LB culture medium. Polyclonal scFv expression plasmids were extracted by using a plasmid extraction kit according to the instructions of the kit. Monoclonal scFv expression plasmids were also extracted after the monoclonal bacteria in shake flasks were cultured overnight, respectively.

(2) Expression and Purification of the Antibody

The polyclonal scFv expression plasmids and the monoclonal scFv expression plasmids were transfected into 293T cells by using PEI respectively. The culture supernatant was collected after 72 hours of transfection. The culture supernatant was mixed with binding buffer in a ratio of 1:1, and then filtered for later use. The Pteoein A column was equilibrated with 5-10 volumes of binding buffer, and the prepared culture supernatant samples were loaded. The column was rinsed with the binding buffer until the binding buffer did not contain the protein. Finally, the eluate was passed through the column, and the eluate was collected until the eluate did not contain the protein. The collected antibody was dialyzed and concentrated.

(3) Detection of Binding of Antibodies by Using the Flow Cytometry

100 μL of suspension of K562 cells expressing CD19 and not expressing CD19 were plated in V cell plates, centrifuged at 500 g for 3 min to precipitate cells. Then the supernatant was discarded. 100 μL of purified antibody solution (IgG concentration was controlled to be 0.5 μg/mL) was added, then incubated at 4° C. for 30 min, centrifuged at 500 g for 3 min, and washed with 200 μL of PBS for three times.

Figure 28:
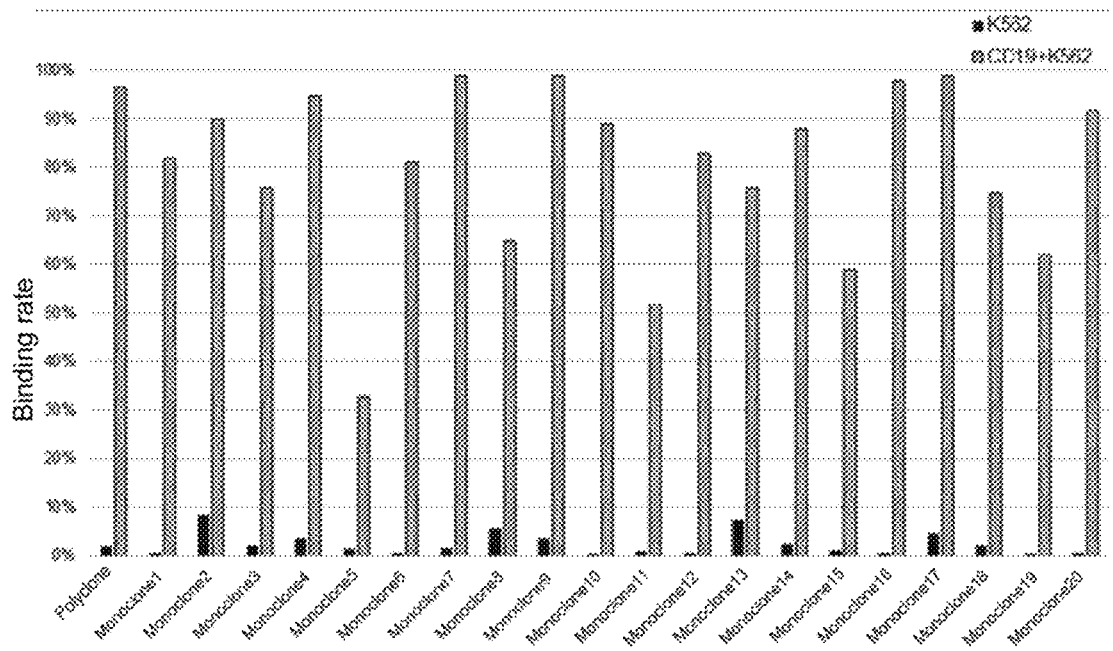
FIG. 28 is a graph showing results of binding efficiency between antibodies screened by the antibody screening method of the present application and antigens, as detected through a flow cytometry according to the present application.

The well was designed according to the experimental. 80 μl of FITC-labeled goat anti-human second antibody (1:150 dilution) was added to each well, then incubated at 4° C. for 30 min, centrifuged at 500 g for 3 min, and after the supernatant was discarded, washed with 200 μL PBS for three times. 200 μL PBS was added to suspend the cells after the last wash. The suspended cells were filtered with a strainer and then detected by the flow cytometry. Results showed that both polyclonal scFv and monoclonal scFv were able to specifically bind to K562 cells expressing the CD19 antigen to varying degrees (FIG. 28). The screened polyclonal scFv and monoclonal scFv were both able to specifically bind to K562 cells expressing the CD19 antigen to varying degrees but not to K562 cells without CD19 antigen expression.

In summary, the present application provides an antibody library construction method and an application thereof. The method is designed based on the principle that a synNotch system controls the gene expression in cells. Through a large number of experiments, the whole scheme flow process is optimized; and after repeated design and verification, the extracellular recognition domain of the synNotch system is changed into an antibody library, and the regulated target gene is changed into a screening marker gene, so that a technology for screening polyclonal antibodies against complex antigens is obtained. In such a way, the problems of complexity, diversity and mutability of tumor antigen and the limited available targets are solved, and this method has a wide application prospect and huge market value.

The applicant has stated that although the detailed method of the present application is described through the examples described above, the present application is not limited to the detailed method described above, which means that implementation of the present application does not necessarily depend on the detailed method described above. It should be apparent to those skilled in the art that any improvements made to the present application, equivalent replacements of raw materials of the product of the present application, additions of adjuvant ingredients to the product of the present application, and selections of specific manners, etc., all fall within the protection scope and the disclosed scope of the present application.

What is claimed is:

1. A method for screening antibody expression cells using drugs, comprising:
   (1) transfecting a vector containing a CIS activator and a screening marker gene combination into a cell and constructing a monoclonal cell line stably transfected with the CIS activator and the screening marker gene combination, wherein the screening marker gene combination comprises a combination of a drug resistance gene, a suicide gene, and a fluorescent protein gene or a molecular tag;
   (2) transfecting antibody gene library expression vectors carrying an extracellular antibody library coding domain, a Notch core domain and an intracellular transcription domain into cells of the monoclonal cell line of the step (1), to obtain a library of antibody expression cells;

(3) expressing the antibody expression cells of step (2), contacting them with an antigen, and adding a screening drug for the drug resistance gene for positive screening of the antibody library expression cells; and (4) adding a screening drug for the suicide gene for negative screening of the screened cells in step (3), to obtain a screened library of antibody expression cells.

2. The method according to claim 1, wherein the drug resistance gene comprises any one or a combination of at least two of a puromycin resistance gene, a neomycin resistance gene, a blasticidin resistance gene, and a hygromycin B resistance gene;

the suicide gene comprises any one or a combination of at least two of a herpes simplex virus thymidine kinase gene, a cytosine deaminase gene, and an iCasp9 suicide system gene;

the fluorescent protein gene comprises any one or a combination of at least two of EGFP, YFP, mCherry, DsRed, and BFP; and the molecular tag comprises any one or a combination of at least two of His-tag, Flag-tag, HA-tag, Myc-tag, and Strep-tag.

3. The method according to claim 1, wherein a screening method for the screening marker gene comprises any one or a combination of at least two of drug screening, flow cytometry detection and sorting, and magnetic-activated cell sorting.

4. The method according to claim 2, wherein a screening drug for the drug resistance gene comprises any one or a combination of at least two of puromycin, G418, blasticidin, and hygromycin B; and a screening drug for the suicide gene comprises any one or a combination of at least two of ganciclovir or FIAU, 5-fluorocytosine, AP1903, and AP20187.

5. The method according to claim 1, wherein a source of the extracellular antibody library coding domain comprises any one or a combination of at least two of an immunized animal, a diseased human population, a healthy human population, a vaccinated human population, and artificial synthesis.

6. The method according to claim 1, wherein the Notch core domain comprises a human Notch, a mouse Notch, or a sequence having a similarity of not less than 85% to the human Notch or the mouse Notch;

wherein the human Notch has an amino acid sequence as shown in SEQ ID NO.1; and the mouse Notch has an amino acid sequence as shown in SEQ ID NO.2.

7. The method according to claim 1, wherein the CIS activator comprises pTet and/or UAS-pSV40.

8. The method according to claim 1, wherein the intracellular transcription domain comprises tTA and/or Gal4-VP64.

9. The method according to claim 1, wherein a method for transfecting comprises any one or a combination of at least two of viral transfection, transfection with a chemical transfection reagent, and electroporation transfection.

10. The method according to claim 1, wherein the antigen comprises any one or a combination of at least two of a wild cell, a cell transfected with a specific antigen gene, a cell bound to a specific antigen, an antigen dissolved in a culture medium, an antigen coated on a culture vessel, an antigen coated on a microsphere, and an antigen coated on a culture scaffold.

* * * * *

SEQUENCE LISTING

```
<160> NUMBER OF SEQ ID NOS: 26

<210> SEQ ID NO 1
<211> LENGTH: 2556
<212> TYPE: PRT
<213> ORGANISM: Artificial sequence
<220> FEATURE:
<223> OTHER INFORMATION: human Notch
<220> FEATURE:
<221> NAME/KEY: misc_feature
<222> LOCATION: (891)..(891)
<223> OTHER INFORMATION: Xaa can be any naturally occurring amino acid

<400> SEQUENCE: 1

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45
```

-continued

Gly Gly Ala Phe Val Gly Pro Arg Cys Gln Asp Pro Asn Pro Cys Leu
         50              55              60

Ser Thr Pro Cys Lys Asn Ala Gly Thr Cys His Val Val Asp Arg Arg
65              70              75              80

Gly Val Ala Asp Tyr Ala Cys Ser Cys Ala Leu Gly Phe Ser Gly Pro
                 85              90              95

Leu Cys Leu Thr Pro Leu Asp Asn Ala Cys Leu Thr Asn Pro Cys Arg
             100             105             110

Asn Gly Gly Thr Cys Asp Leu Leu Thr Leu Thr Glu Tyr Lys Cys Arg
             115             120             125

Cys Pro Pro Gly Trp Ser Gly Lys Ser Cys Gln Gln Ala Asp Pro Cys
         130             135             140

Ala Ser Asn Pro Cys Ala Asn Gly Gly Gln Cys Leu Pro Phe Glu Ala
145             150             155             160

Ser Tyr Ile Cys His Cys Pro Pro Ser Phe His Gly Pro Thr Cys Arg
                 165             170             175

Gln Asp Val Asn Glu Cys Gly Gln Lys Pro Arg Leu Cys Arg His Gly
             180             185             190

Gly Thr Cys His Asn Glu Val Gly Ser Tyr Arg Cys Val Cys Arg Ala
         195             200             205

Thr His Thr Gly Pro Asn Cys Glu Arg Pro Tyr Val Pro Cys Ser Pro
         210             215             220

Ser Pro Cys Gln Asn Gly Gly Thr Cys Arg Pro Thr Gly Asp Val Thr
225             230             235             240

His Glu Cys Ala Cys Leu Pro Gly Phe Thr Gly Gln Asn Cys Glu Glu
                 245             250             255

Asn Ile Asp Asp Cys Pro Gly Asn Asn Cys Lys Asn Gly Gly Ala Cys
             260             265             270

Val Asp Gly Val Asn Thr Tyr Asn Cys Pro Cys Pro Pro Glu Trp Thr
         275             280             285

Gly Gln Tyr Cys Thr Glu Asp Val Asp Glu Cys Gln Leu Met Pro Asn
         290             295             300

Ala Cys Gln Asn Gly Gly Thr Cys His Asn Thr His Gly Gly Tyr Asn
305             310             315             320

Cys Val Cys Val Asn Gly Trp Thr Gly Glu Asp Cys Ser Glu Asn Ile
                 325             330             335

Asp Asp Cys Ala Ser Ala Ala Cys Phe His Gly Ala Thr Cys His Asp
             340             345             350

Arg Val Ala Ser Phe Tyr Cys Glu Cys Pro His Gly Arg Thr Gly Leu
         355             360             365

Leu Cys His Leu Asn Asp Ala Cys Ile Ser Asn Pro Cys Asn Glu Gly
         370             375             380

Ser Asn Cys Asp Thr Asn Pro Val Asn Gly Lys Ala Ile Cys Thr Cys
385             390             395             400

Pro Ser Gly Tyr Thr Gly Pro Ala Cys Ser Gln Asp Val Asp Glu Cys
                 405             410             415

Ser Leu Gly Ala Asn Pro Cys Glu His Ala Gly Lys Cys Ile Asn Thr
             420             425             430

Leu Gly Ser Phe Glu Cys Gln Cys Leu Gln Gly Tyr Thr Gly Pro Arg
         435             440             445

Cys Glu Ile Asp Val Asn Glu Cys Val Ser Asn Pro Cys Gln Asn Asp
         450             455             460

-continued

```
Ala Thr Cys Leu Asp Gln Ile Gly Glu Phe Gln Cys Met Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
        595                 600                 605

Ser Gln Pro Cys Arg Leu Arg Gly Thr Cys Gln Asp Pro Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ser Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Ile Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Lys Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
        835                 840                 845

Asp Tyr Glu Ser Phe Ser Cys Val Cys Pro Thr Gly Ala Lys Gly
    850                 855                 860

Gln Thr Cys Glu Val Asp Ile Asn Glu Cys Val Leu Ser Pro Cys Arg
865                 870                 875                 880

His Gly Ala Ser Cys Gln Asn Thr His Gly Xaa Tyr Arg Cys His Cys
```

```
                885                 890                 895
Gln Ala Gly Tyr Ser Gly Arg Asn Cys Glu Thr Asp Ile Asp Asp Cys
                    900                 905                 910
Arg Pro Asn Pro Cys His Asn Gly Gly Ser Cys Thr Asp Gly Ile Asn
                915                 920                 925
Thr Ala Phe Cys Asp Cys Leu Pro Gly Phe Arg Gly Thr Phe Cys Glu
            930                 935                 940
Glu Asp Ile Asn Glu Cys Ala Ser Asp Pro Cys Arg Asn Gly Ala Asn
945                 950                 955                 960
Cys Thr Asp Cys Val Asp Ser Tyr Thr Cys Thr Cys Pro Ala Gly Phe
                965                 970                 975
Ser Gly Ile His Cys Glu Asn Asn Thr Pro Asp Cys Thr Glu Ser Ser
            980                 985                 990
Cys Phe Asn Gly Gly Thr Cys Val Asp Gly Ile Asn Ser Phe Thr Cys
            995                 1000                1005
Leu Cys Pro Pro Gly Phe Thr Gly Ser Tyr Cys Gln His Val Val
        1010                1015                1020
Asn Glu Cys Asp Ser Arg Pro Cys Leu Leu Gly Thr Cys Gln
        1025                1030                1035
Asp Gly Arg Gly Leu His Arg Cys Thr Cys Pro Gln Gly Tyr Thr
        1040                1045                1050
Gly Pro Asn Cys Gln Asn Leu Val His Trp Cys Asp Ser Ser Pro
        1055                1060                1065
Cys Lys Asn Gly Gly Lys Cys Trp Gln Thr His Thr Gln Tyr Arg
        1070                1075                1080
Cys Glu Cys Pro Ser Gly Trp Thr Gly Leu Tyr Cys Asp Val Pro
        1085                1090                1095
Ser Val Ser Cys Glu Val Ala Ala Gln Arg Gln Gly Val Asp Val
        1100                1105                1110
Ala Arg Leu Cys Gln His Gly Gly Leu Cys Val Asp Ala Gly Asn
        1115                1120                1125
Thr His His Cys Arg Cys Gln Ala Gly Tyr Thr Gly Ser Tyr Cys
        1130                1135                1140
Glu Asp Leu Val Asp Glu Cys Ser Pro Ser Pro Cys Gln Asn Gly
        1145                1150                1155
Ala Thr Cys Thr Asp Tyr Leu Gly Gly Tyr Ser Cys Lys Cys Val
        1160                1165                1170
Ala Gly Tyr His Gly Val Asn Cys Ser Glu Glu Ile Asp Glu Cys
        1175                1180                1185
Leu Ser His Pro Cys Gln Asn Gly Gly Thr Cys Leu Asp Leu Pro
        1190                1195                1200
Asn Thr Tyr Lys Cys Ser Cys Pro Arg Gly Thr Gln Gly Val His
        1205                1210                1215
Cys Glu Ile Asn Val Asp Asp Cys Asn Pro Pro Val Asp Pro Val
        1220                1225                1230
Ser Arg Ser Pro Lys Cys Phe Asn Asn Gly Thr Cys Val Asp Gln
        1235                1240                1245
Val Gly Gly Tyr Ser Cys Thr Cys Pro Pro Gly Phe Val Gly Glu
        1250                1255                1260
Arg Cys Glu Gly Asp Val Asn Glu Cys Leu Ser Asn Pro Cys Asp
        1265                1270                1275
Ala Arg Gly Thr Gln Asn Cys Val Gln Arg Val Asn Asp Phe His
        1280                1285                1290
```

```
Cys Glu Cys Arg Ala Gly His Thr Gly Arg Arg Cys Glu Ser Val
    1295                1300                1305

Ile Asn Gly Cys Lys Gly Lys Pro Cys Lys Asn Gly Gly Thr Cys
    1310                1315                1320

Ala Val Ala Ser Asn Thr Ala Arg Gly Phe Ile Cys Lys Cys Pro
    1325                1330                1335

Ala Gly Phe Glu Gly Ala Thr Cys Glu Asn Asp Ala Arg Thr Cys
    1340                1345                1350

Gly Ser Leu Arg Cys Leu Asn Gly Gly Thr Cys Ile Ser Gly Pro
    1355                1360                1365

Arg Ser Pro Thr Cys Leu Cys Leu Gly Pro Phe Thr Gly Pro Glu
    1370                1375                1380

Cys Gln Phe Pro Ala Ser Ser Pro Cys Leu Gly Gly Asn Pro Cys
    1385                1390                1395

Tyr Asn Gln Gly Thr Cys Glu Pro Thr Ser Glu Ser Pro Phe Tyr
    1400                1405                1410

Arg Cys Leu Cys Pro Ala Lys Phe Asn Gly Leu Leu Cys His Ile
    1415                1420                1425

Leu Asp Tyr Ser Phe Gly Gly Gly Ala Gly Arg Asp Ile Pro Pro
    1430                1435                1440

Pro Leu Ile Glu Glu Ala Cys Glu Leu Pro Glu Cys Gln Glu Asp
    1445                1450                1455

Ala Gly Asn Lys Val Cys Ser Leu Gln Cys Asn Asn His Ala Cys
    1460                1465                1470

Gly Trp Asp Gly Gly Asp Cys Ser Leu Asn Phe Asn Asp Pro Trp
    1475                1480                1485

Lys Asn Cys Thr Gln Ser Leu Gln Cys Trp Lys Tyr Phe Ser Asp
    1490                1495                1500

Gly His Cys Asp Ser Gln Cys Asn Ser Ala Gly Cys Leu Phe Asp
    1505                1510                1515

Gly Phe Asp Cys Gln Arg Ala Glu Gly Gln Cys Asn Pro Leu Tyr
    1520                1525                1530

Asp Gln Tyr Cys Lys Asp His Phe Ser Asp Gly His Cys Asp Gln
    1535                1540                1545

Gly Cys Asn Ser Ala Glu Cys Glu Trp Asp Gly Leu Asp Cys Ala
    1550                1555                1560

Glu His Val Pro Glu Arg Leu Ala Ala Gly Thr Leu Val Val Val
    1565                1570                1575

Val Leu Met Pro Pro Glu Gln Leu Arg Asn Ser Ser Phe His Phe
    1580                1585                1590

Leu Arg Glu Leu Ser Arg Val Leu His Thr Asn Val Val Phe Lys
    1595                1600                1605

Arg Asp Ala His Gly Gln Gln Met Ile Phe Pro Tyr Tyr Gly Arg
    1610                1615                1620

Glu Glu Glu Leu Arg Lys His Pro Ile Lys Arg Ala Ala Glu Gly
    1625                1630                1635

Trp Ala Ala Pro Asp Ala Leu Leu Gly Gln Val Lys Ala Ser Leu
    1640                1645                1650

Leu Pro Gly Gly Ser Glu Gly Gly Arg Arg Arg Glu Leu Asp
    1655                1660                1665

Pro Met Asp Val Arg Gly Ser Ile Val Tyr Leu Glu Ile Asp Asn
    1670                1675                1680
```

```
Arg Gln Cys Val Gln Ala Ser Ser Gln Cys Phe Gln Ser Ala Thr
    1685                1690                1695

Asp Val Ala Ala Phe Leu Gly Ala Leu Ala Ser Leu Gly Ser Leu
    1700                1705                1710

Asn Ile Pro Tyr Lys Ile Glu Ala Val Gln Ser Glu Thr Val Glu
    1715                1720                1725

Pro Pro Pro Pro Ala Gln Leu His Phe Met Tyr Val Ala Ala Ala
    1730                1735                1740

Ala Phe Val Leu Leu Phe Phe Val Gly Cys Gly Val Leu Leu Ser
    1745                1750                1755

Arg Lys Arg Arg Arg Gln His Gly Gln Leu Trp Phe Pro Glu Gly
    1760                1765                1770

Phe Lys Val Ser Glu Ala Ser Lys Lys Lys Arg Arg Glu Pro Leu
    1775                1780                1785

Gly Glu Asp Ser Val Gly Leu Lys Pro Leu Lys Asn Ala Ser Asp
    1790                1795                1800

Gly Ala Leu Met Asp Asp Asn Gln Asn Glu Trp Gly Asp Glu Asp
    1805                1810                1815

Leu Glu Thr Lys Lys Phe Arg Phe Glu Glu Pro Val Val Leu Pro
    1820                1825                1830

Asp Leu Asp Asp Gln Thr Asp His Arg Gln Trp Thr Gln Gln His
    1835                1840                1845

Leu Asp Ala Ala Asp Leu Arg Met Ser Ala Met Ala Pro Thr Pro
    1850                1855                1860

Pro Gln Gly Glu Val Asp Ala Asp Cys Met Asp Val Asn Val Arg
    1865                1870                1875

Gly Pro Asp Gly Phe Thr Pro Leu Met Ile Ala Ser Cys Ser Gly
    1880                1885                1890

Gly Gly Leu Glu Thr Gly Asn Ser Glu Glu Glu Asp Ala Pro
    1895                1900                1905

Ala Val Ile Ser Asp Phe Ile Tyr Gln Gly Ala Ser Leu His Asn
    1910                1915                1920

Gln Thr Asp Arg Thr Gly Glu Thr Ala Leu His Leu Ala Ala Arg
    1925                1930                1935

Tyr Ser Arg Ser Asp Ala Ala Lys Arg Leu Leu Glu Ala Ser Ala
    1940                1945                1950

Asp Ala Asn Ile Gln Asp Asn Met Gly Arg Thr Pro Leu His Ala
    1955                1960                1965

Ala Val Ser Ala Asp Ala Gln Gly Val Phe Gln Ile Leu Ile Arg
    1970                1975                1980

Asn Arg Ala Thr Asp Leu Asp Ala Arg Met His Asp Gly Thr Thr
    1985                1990                1995

Pro Leu Ile Leu Ala Ala Arg Leu Ala Val Glu Gly Met Leu Glu
    2000                2005                2010

Asp Leu Ile Asn Ser His Ala Asp Val Asn Ala Val Asp Asp Leu
    2015                2020                2025

Gly Lys Ser Ala Leu His Trp Ala Ala Ala Val Asn Asn Val Asp
    2030                2035                2040

Ala Ala Val Val Leu Leu Lys Asn Gly Ala Asn Lys Asp Met Gln
    2045                2050                2055

Asn Asn Arg Glu Glu Thr Pro Leu Phe Leu Ala Ala Arg Glu Gly
    2060                2065                2070

Ser Tyr Glu Thr Ala Lys Val Leu Leu Asp His Phe Ala Asn Arg
```

```
              2075                2080                2085

Asp Ile Thr Asp His Met Asp Arg Leu Pro Arg Asp Ile Ala Gln
        2090                2095                2100

Glu Arg Met His His Asp Ile Val Arg Leu Leu Asp Glu Tyr Asn
        2105                2110                2115

Leu Val Arg Ser Pro Gln Leu His Gly Ala Pro Leu Gly Gly Thr
        2120                2125                2130

Pro Thr Leu Ser Pro Pro Leu Cys Ser Pro Asn Gly Tyr Leu Gly
        2135                2140                2145

Ser Leu Lys Pro Gly Val Gln Gly Lys Lys Val Arg Lys Pro Ser
        2150                2155                2160

Ser Lys Gly Leu Ala Cys Gly Ser Lys Glu Ala Lys Asp Leu Lys
        2165                2170                2175

Ala Arg Arg Lys Lys Ser Gln Asp Gly Lys Gly Cys Leu Leu Asp
        2180                2185                2190

Ser Ser Gly Met Leu Ser Pro Val Asp Ser Leu Glu Ser Pro His
        2195                2200                2205

Gly Tyr Leu Ser Asp Val Ala Ser Pro Pro Leu Leu Pro Ser Pro
        2210                2215                2220

Phe Gln Gln Ser Pro Ser Val Pro Leu Asn His His Leu Pro Gly Met
        2225                2230                2235

Pro Asp Thr His Leu Gly Ile Gly His Leu Asn Val Ala Ala Lys
        2240                2245                2250

Pro Glu Met Ala Ala Leu Gly Gly Gly Arg Leu Ala Phe Glu
        2255                2260                2265

Thr Gly Pro Pro Arg Leu Ser His Leu Pro Val Ala Ser Gly Thr
        2270                2275                2280

Ser Thr Val Leu Gly Ser Ser Ser Gly Gly Ala Leu Asn Phe Thr
        2285                2290                2295

Val Gly Gly Ser Thr Ser Leu Asn Gly Gln Cys Glu Trp Leu Ser
        2300                2305                2310

Arg Leu Gln Ser Gly Met Val Pro Asn Gln Tyr Asn Pro Leu Arg
        2315                2320                2325

Gly Ser Val Ala Pro Gly Pro Leu Ser Thr Gln Ala Pro Ser Leu
        2330                2335                2340

Gln His Gly Met Val Gly Pro Leu His Ser Ser Leu Ala Ala Ser
        2345                2350                2355

Ala Leu Ser Gln Met Met Ser Tyr Gln Gly Leu Pro Ser Thr Arg
        2360                2365                2370

Leu Ala Thr Gln Pro His Leu Val Gln Thr Gln Val Gln Pro
        2375                2380                2385

Gln Asn Leu Gln Met Gln Gln Gln Asn Leu Gln Pro Ala Asn Ile
        2390                2395                2400

Gln Gln Gln Gln Ser Leu Gln Pro Pro Pro Pro Pro Gln Pro
        2405                2410                2415

His Leu Gly Val Ser Ser Ala Ala Ser Gly His Leu Gly Arg Ser
        2420                2425                2430

Phe Leu Ser Gly Glu Pro Ser Gln Ala Asp Val Gln Pro Leu Gly
        2435                2440                2445

Pro Ser Ser Leu Ala Val His Thr Ile Leu Pro Gln Glu Ser Pro
        2450                2455                2460

Ala Leu Pro Thr Ser Leu Pro Ser Ser Leu Val Pro Pro Val Thr
        2465                2470                2475
```

```
Ala  Ala  Gln  Phe  Leu  Thr  Pro  Pro  Ser  Gln  His  Ser  Tyr  Ser  Ser
     2480           2485               2490

Pro  Val  Asp  Asn  Thr  Pro  Ser  His  Gln  Leu  Gln  Val  Pro  Glu  His
     2495           2500               2505

Pro  Phe  Leu  Thr  Pro  Ser  Pro  Glu  Ser  Pro  Asp  Gln  Trp  Ser  Ser
     2510           2515               2520

Ser  Ser  Pro  His  Ser  Asn  Val  Ser  Asp  Trp  Ser  Glu  Gly  Val  Ser
     2525           2530               2535

Ser  Pro  Pro  Thr  Ser  Met  Gln  Ser  Gln  Ile  Ala  Arg  Ile  Pro  Glu
     2540           2545               2550

Ala  Phe  Lys
     2555

<210> SEQ ID NO 2
<211> LENGTH: 2531
<212> TYPE: PRT
<213> ORGANISM: Artificial sequence
<220> FEATURE:
<223> OTHER INFORMATION: mouse Notch

<400> SEQUENCE: 2

Met  Pro  Arg  Leu  Leu  Thr  Pro  Leu  Leu  Cys  Leu  Thr  Leu  Leu  Pro  Ala
1                 5                        10                       15

Leu  Ala  Ala  Arg  Gly  Leu  Arg  Cys  Ser  Gln  Pro  Ser  Gly  Thr  Cys  Leu
                20                       25                       30

Asn  Gly  Gly  Arg  Cys  Glu  Val  Ala  Asn  Gly  Thr  Glu  Ala  Cys  Val  Cys
                35                       40                       45

Ser  Gly  Ala  Phe  Val  Gly  Gln  Arg  Cys  Gln  Asp  Ser  Asn  Pro  Cys  Leu
     50                       55                       60

Ser  Thr  Pro  Cys  Lys  Asn  Ala  Gly  Thr  Cys  His  Val  Val  Asp  His  Gly
65                       70                       75                       80

Gly  Thr  Val  Asp  Tyr  Ala  Cys  Ser  Cys  Pro  Leu  Gly  Phe  Ser  Gly  Pro
                85                       90                       95

Leu  Cys  Leu  Thr  Pro  Leu  Asp  Asn  Ala  Cys  Leu  Ala  Asn  Pro  Cys  Arg
                100                      105                      110

Asn  Gly  Gly  Thr  Cys  Asp  Leu  Leu  Thr  Leu  Thr  Glu  Tyr  Lys  Cys  Arg
                115                      120                      125

Cys  Pro  Pro  Gly  Trp  Ser  Gly  Lys  Ser  Cys  Gln  Gln  Ala  Asp  Pro  Cys
     130                      135                      140

Ala  Ser  Asn  Pro  Cys  Ala  Asn  Gly  Gly  Gln  Cys  Leu  Pro  Phe  Glu  Ser
145                      150                      155                      160

Ser  Tyr  Ile  Cys  Arg  Cys  Pro  Pro  Gly  Phe  His  Gly  Pro  Thr  Cys  Arg
                165                      170                      175

Gln  Asp  Val  Asn  Glu  Cys  Ser  Gln  Asn  Pro  Gly  Leu  Cys  Arg  His  Gly
                180                      185                      190

Gly  Thr  Cys  His  Asn  Glu  Ile  Gly  Ser  Tyr  Arg  Cys  Ala  Cys  Arg  Ala
                195                      200                      205

Thr  His  Thr  Gly  Pro  His  Cys  Glu  Leu  Pro  Tyr  Val  Pro  Cys  Ser  Pro
     210                      215                      220

Ser  Pro  Cys  Gln  Asn  Gly  Gly  Thr  Cys  Arg  Pro  Thr  Gly  Asp  Thr  Thr
225                      230                      235                      240

His  Glu  Cys  Ala  Cys  Leu  Pro  Gly  Phe  Ala  Gly  Gln  Asn  Cys  Glu  Glu
                245                      250                      255

Asn  Val  Asp  Asp  Cys  Pro  Gly  Asn  Asn  Cys  Lys  Asn  Gly  Gly  Ala  Cys
                260                      265                      270
```

```
Val Asp Gly Val Asn Thr Tyr Asn Cys Arg Cys Pro Pro Glu Trp Thr
            275                 280                 285

Gly Gln Tyr Cys Thr Glu Asp Val Asp Glu Cys Gln Leu Met Pro Asn
        290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
            325                 330                 335

Asp Asp Cys Ala Ser Ala Ala Cys Phe Gln Gly Ala Thr Cys His Asp
            340                 345                 350

Arg Val Ala Ser Phe Tyr Cys Glu Cys Pro His Gly Arg Thr Gly Leu
            355                 360                 365

Leu Cys His Leu Asn Asp Ala Cys Ile Ser Asn Pro Cys Asn Glu Gly
            370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
            405                 410                 415

Ala Leu Gly Ala Asn Pro Cys Glu His Ala Gly Lys Cys Leu Asn Thr
            420                 425                 430

Leu Gly Ser Phe Glu Cys Gln Cys Leu Gln Gly Tyr Thr Gly Pro Arg
            435                 440                 445

Cys Glu Ile Asp Val Asn Glu Cys Ile Ser Asn Pro Cys Gln Asn Asp
            450                 455                 460

Ala Thr Cys Leu Asp Gln Ile Gly Glu Phe Gln Cys Ile Cys Met Pro
465                 470                 475                 480

Gly Tyr Glu Gly Val Tyr Cys Glu Ile Asn Thr Asp Glu Cys Ala Ser
            485                 490                 495

Ser Pro Cys Leu His Asn Gly His Cys Met Asp Lys Ile Asn Glu Phe
            500                 505                 510

Gln Cys Gln Cys Pro Lys Gly Phe Asn Gly His Leu Cys Gln Tyr Asp
            515                 520                 525

Val Asp Glu Cys Ala Ser Thr Pro Cys Lys Asn Gly Ala Lys Cys Leu
            530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
            565                 570                 575

Tyr Gly Ser Cys Lys Asp Gly Val Ala Thr Phe Thr Cys Leu Cys Gln
            580                 585                 590

Pro Gly Tyr Thr Gly His His Cys Glu Thr Asn Ile Asn Glu Cys His
            595                 600                 605

Ser Gln Pro Cys Arg His Gly Gly Thr Cys Gln Asp Arg Asp Asn Ser
            610                 615                 620

Tyr Leu Cys Leu Cys Leu Lys Gly Thr Thr Gly Pro Asn Cys Glu Ile
625                 630                 635                 640

Asn Leu Asp Asp Cys Ala Ser Asn Pro Cys Asp Ser Gly Thr Cys Leu
            645                 650                 655

Asp Lys Ile Asp Gly Tyr Glu Cys Ala Cys Glu Pro Gly Tyr Thr Gly
            660                 665                 670

Ser Met Cys Asn Val Asn Ile Asp Glu Cys Ala Gly Ser Pro Cys His
            675                 680                 685
```

-continued

```
Asn Gly Gly Thr Cys Glu Asp Gly Ile Ala Gly Phe Thr Cys Arg Cys
690                 695                 700
Pro Glu Gly Tyr His Asp Pro Thr Cys Leu Ser Glu Val Asn Glu Cys
705                 710                 715                 720
Asn Ser Asn Pro Cys Ile His Gly Ala Cys Arg Asp Gly Leu Asn Gly
                725                 730                 735
Tyr Lys Cys Asp Cys Ala Pro Gly Trp Ser Gly Thr Asn Cys Asp Ile
                740                 745                 750
Asn Asn Asn Glu Cys Glu Ser Asn Pro Cys Val Asn Gly Gly Thr Cys
            755                 760                 765
Lys Asp Met Thr Ser Gly Tyr Val Cys Thr Cys Arg Glu Gly Phe Ser
770                 775                 780
Gly Pro Asn Cys Gln Thr Asn Ile Asn Glu Cys Ala Ser Asn Pro Cys
785                 790                 795                 800
Leu Asn Gln Gly Thr Cys Ile Asp Asp Val Ala Gly Tyr Lys Cys Asn
                805                 810                 815
Cys Pro Leu Pro Tyr Thr Gly Ala Thr Cys Glu Val Val Leu Ala Pro
                820                 825                 830
Cys Ala Thr Ser Pro Cys Lys Asn Ser Gly Val Cys Lys Glu Ser Glu
                835                 840                 845
Asp Tyr Glu Ser Phe Ser Cys Val Cys Pro Thr Gly Trp Gln Gly Gln
850                 855                 860
Thr Cys Glu Val Asp Ile Asn Glu Cys Val Lys Ser Pro Cys Arg His
865                 870                 875                 880
Gly Ala Ser Cys Gln Asn Thr Asn Gly Ser Tyr Arg Cys Leu Cys Gln
                885                 890                 895
Ala Gly Tyr Thr Gly Arg Asn Cys Glu Ser Asp Ile Asp Asp Cys Arg
                900                 905                 910
Pro Asn Pro Cys His Asn Gly Gly Ser Cys Thr Asp Gly Ile Asn Thr
                915                 920                 925
Ala Phe Cys Asp Cys Leu Pro Gly Phe Gln Gly Ala Phe Cys Glu Glu
                930                 935                 940
Asp Ile Asn Glu Cys Ala Ser Asn Pro Cys Gln Asn Gly Ala Asn Cys
945                 950                 955                 960
Thr Asp Cys Val Asp Ser Tyr Thr Cys Thr Cys Pro Val Gly Phe Asn
                965                 970                 975
Gly Ile His Cys Glu Asn Asn Thr Pro Asp Cys Thr Glu Ser Ser Cys
                980                 985                 990
Phe Asn Gly Gly Thr Cys Val Asp Gly Ile Asn Ser Phe Thr Cys Leu
                995                 1000                1005
Cys Pro Pro Gly Phe Thr Gly Ser Tyr Cys Gln Tyr Asp Val Asn
                1010                1015                1020
Glu Cys Asp Ser Arg Pro Cys Leu His Gly Gly Thr Cys Gln Asp
            1025                1030                1035
Ser Tyr Gly Thr Tyr Lys Cys Thr Cys Pro Gln Gly Tyr Thr Gly
            1040                1045                1050
Leu Asn Cys Gln Asn Leu Val Arg Trp Cys Asp Ser Ala Pro Cys
            1055                1060                1065
Lys Asn Gly Gly Arg Cys Trp Gln Thr Asn Thr Gln Tyr His Cys
            1070                1075                1080
Glu Cys Arg Ser Gly Trp Thr Gly Val Asn Cys Asp Val Leu Ser
            1085                1090                1095
Val Ser Cys Glu Val Ala Ala Gln Lys Arg Gly Ile Asp Val Thr
```

-continued

```
                1100                1105                1110
Leu Leu Cys Gln His Gly Gly Leu Cys Val Asp Glu Gly Asp Lys
        1115                1120                1125
His Tyr Cys His Cys Gln Ala Gly Tyr Thr Gly Ser Tyr Cys Glu
        1130                1135                1140
Asp Glu Val Asp Glu Cys Ser Pro Asn Pro Cys Gln Asn Gly Ala
        1145                1150                1155
Thr Cys Thr Asp Tyr Leu Gly Gly Phe Ser Cys Lys Cys Val Ala
        1160                1165                1170
Gly Tyr His Gly Ser Asn Cys Ser Glu Glu Ile Asn Glu Cys Leu
        1175                1180                1185
Ser Gln Pro Cys Gln Asn Gly Gly Thr Cys Ile Asp Leu Thr Asn
        1190                1195                1200
Ser Tyr Lys Cys Ser Cys Pro Arg Gly Thr Gln Gly Val His Cys
        1205                1210                1215
Glu Ile Asn Val Asp Asp Cys His Pro Pro Leu Asp Pro Ala Ser
        1220                1225                1230
Arg Ser Pro Lys Cys Phe Asn Asn Gly Thr Cys Val Asp Gln Val
        1235                1240                1245
Gly Gly Tyr Thr Cys Thr Cys Pro Pro Gly Phe Val Gly Glu Arg
        1250                1255                1260
Cys Glu Gly Asp Val Asn Glu Cys Leu Ser Asn Pro Cys Asp Pro
        1265                1270                1275
Arg Gly Thr Gln Asn Cys Val Gln Arg Val Asn Asp Phe His Cys
        1280                1285                1290
Glu Cys Arg Ala Gly His Thr Gly Arg Arg Cys Glu Ser Val Ile
        1295                1300                1305
Asn Gly Cys Arg Gly Lys Pro Cys Lys Asn Gly Gly Val Cys Ala
        1310                1315                1320
Val Ala Ser Asn Thr Ala Arg Gly Phe Ile Cys Arg Cys Pro Ala
        1325                1330                1335
Gly Phe Glu Gly Ala Thr Cys Glu Asn Asp Ala Arg Thr Cys Gly
        1340                1345                1350
Ser Leu Arg Cys Leu Asn Gly Gly Thr Cys Ile Ser Gly Pro Arg
        1355                1360                1365
Ser Pro Thr Cys Leu Cys Leu Gly Ser Phe Thr Gly Pro Glu Cys
        1370                1375                1380
Gln Phe Pro Ala Ser Ser Pro Cys Val Gly Ser Asn Pro Cys Tyr
        1385                1390                1395
Asn Gln Gly Thr Cys Glu Pro Thr Ser Glu Asn Pro Phe Tyr Arg
        1400                1405                1410
Cys Leu Cys Pro Ala Lys Phe Asn Gly Leu Leu Cys His Ile Leu
        1415                1420                1425
Asp Tyr Ser Phe Thr Gly Gly Ala Gly Arg Asp Ile Pro Pro Pro
        1430                1435                1440
Gln Ile Glu Glu Ala Cys Glu Leu Pro Glu Cys Gln Val Asp Ala
        1445                1450                1455
Gly Asn Lys Val Cys Asn Leu Gln Cys Asn Asn His Ala Cys Gly
        1460                1465                1470
Trp Asp Gly Gly Asp Cys Ser Leu Asn Phe Asn Asp Pro Trp Lys
        1475                1480                1485
Asn Cys Thr Gln Ser Leu Gln Cys Trp Lys Tyr Phe Ser Asp Gly
        1490                1495                1500
```

```
His Cys Asp Ser Gln Cys Asn Ser Ala Gly Cys Leu Phe Asp Gly
1505                1510                1515

Phe Asp Cys Gln Leu Thr Glu Gly Gln Cys Asn Pro Leu Tyr Asp
1520                1525                1530

Gln Tyr Cys Lys Asp His Phe Ser Asp Gly His Cys Asp Gln Gly
1535                1540                1545

Cys Asn Ser Ala Glu Cys Glu Trp Asp Gly Leu Asp Cys Ala Glu
1550                1555                1560

His Val Pro Glu Arg Leu Ala Ala Gly Thr Leu Val Leu Val Val
1565                1570                1575

Leu Leu Pro Pro Asp Gln Leu Arg Asn Asn Ser Phe His Phe Leu
1580                1585                1590

Arg Glu Leu Ser His Val Leu His Thr Asn Val Val Phe Lys Arg
1595                1600                1605

Asp Ala Gln Gly Gln Gln Met Ile Phe Pro Tyr Tyr Gly His Glu
1610                1615                1620

Glu Glu Leu Arg Lys His Pro Ile Lys Arg Ser Thr Val Gly Trp
1625                1630                1635

Ala Thr Ser Ser Leu Leu Pro Gly Thr Ser Gly Gly Arg Gln Arg
1640                1645                1650

Arg Glu Leu Asp Pro Met Asp Ile Arg Gly Ser Ile Val Tyr Leu
1655                1660                1665

Glu Ile Asp Asn Arg Gln Cys Val Gln Ser Ser Ser Gln Cys Phe
1670                1675                1680

Gln Ser Ala Thr Asp Val Ala Ala Phe Leu Gly Ala Leu Ala Ser
1685                1690                1695

Leu Gly Ser Leu Asn Ile Pro Tyr Lys Ile Glu Ala Val Lys Ser
1700                1705                1710

Glu Pro Val Glu Pro Pro Leu Pro Ser Gln Leu His Leu Met Tyr
1715                1720                1725

Val Ala Ala Ala Ala Phe Val Leu Leu Phe Phe Val Gly Cys Gly
1730                1735                1740

Val Leu Leu Ser Arg Lys Arg Arg Arg Gln His Gly Gln Leu Trp
1745                1750                1755

Phe Pro Glu Gly Phe Lys Val Ser Glu Ala Ser Lys Lys Lys Arg
1760                1765                1770

Arg Glu Pro Leu Gly Glu Asp Ser Val Gly Leu Lys Pro Leu Lys
1775                1780                1785

Asn Ala Ser Asp Gly Ala Leu Met Asp Asp Asn Gln Asn Glu Trp
1790                1795                1800

Gly Asp Glu Asp Leu Glu Thr Lys Lys Phe Arg Phe Glu Glu Pro
1805                1810                1815

Val Val Leu Pro Asp Leu Ser Asp Gln Thr Asp His Arg Gln Trp
1820                1825                1830

Thr Gln Gln His Leu Asp Ala Ala Asp Leu Arg Met Ser Ala Met
1835                1840                1845

Ala Pro Thr Pro Pro Gln Gly Glu Val Asp Ala Asp Cys Met Asp
1850                1855                1860

Val Asn Val Arg Gly Pro Asp Gly Phe Thr Pro Leu Met Ile Ala
1865                1870                1875

Ser Cys Ser Gly Gly Gly Leu Glu Thr Gly Asn Ser Glu Glu Glu
1880                1885                1890
```

```
Glu Asp Ala Pro Ala Val Ile Ser Asp Phe Ile Tyr Gln Gly Ala
1895                1900                1905

Ser Leu His Asn Gln Thr Asp Arg Thr Gly Glu Thr Ala Leu His
1910                1915                1920

Leu Ala Ala Arg Tyr Ser Arg Ser Asp Ala Ala Lys Arg Leu Leu
1925                1930                1935

Glu Ala Ser Ala Asp Ala Asn Ile Gln Asp Asn Met Gly Arg Thr
1940                1945                1950

Pro Leu His Ala Ala Val Ser Ala Asp Ala Gln Gly Val Phe Gln
1955                1960                1965

Ile Leu Leu Arg Asn Arg Ala Thr Asp Leu Asp Ala Arg Met His
1970                1975                1980

Asp Gly Thr Thr Pro Leu Ile Leu Ala Ala Arg Leu Ala Val Glu
1985                1990                1995

Gly Met Leu Glu Asp Leu Ile Asn Ser His Ala Asp Val Asn Ala
2000                2005                2010

Val Asp Asp Leu Gly Lys Ser Ala Leu His Trp Ala Ala Ala Val
2015                2020                2025

Asn Asn Val Asp Ala Ala Val Val Leu Leu Lys Asn Gly Ala Asn
2030                2035                2040

Lys Asp Met Gln Asn Asn Lys Glu Glu Thr Pro Leu Phe Leu Ala
2045                2050                2055

Ala Arg Glu Gly Ser Tyr Glu Thr Ala Lys Val Leu Leu Asp His
2060                2065                2070

Phe Ala Asn Arg Asp Ile Thr Asp His Met Asp Arg Leu Pro Arg
2075                2080                2085

Asp Ile Ala Gln Glu Arg Met His His Asp Ile Val Arg Leu Leu
2090                2095                2100

Asp Glu Tyr Asn Leu Val Arg Ser Pro Gln Leu His Gly Thr Ala
2105                2110                2115

Leu Gly Gly Thr Pro Thr Leu Ser Pro Thr Leu Cys Ser Pro Asn
2120                2125                2130

Gly Tyr Leu Gly Asn Leu Lys Ser Ala Thr Gln Gly Lys Lys Ala
2135                2140                2145

Arg Lys Pro Ser Thr Lys Gly Leu Ala Cys Gly Ser Lys Glu Ala
2150                2155                2160

Lys Asp Leu Lys Ala Arg Arg Lys Lys Ser Gln Asp Gly Lys Gly
2165                2170                2175

Cys Leu Leu Asp Ser Ser Ser Met Leu Ser Pro Val Asp Ser Leu
2180                2185                2190

Glu Ser Pro His Gly Tyr Leu Ser Asp Val Ala Ser Pro Pro Leu
2195                2200                2205

Leu Pro Ser Pro Phe Gln Gln Ser Pro Ser Met Pro Leu Ser His
2210                2215                2220

Leu Pro Gly Met Pro Asp Thr His Leu Gly Ile Ser His Leu Asn
2225                2230                2235

Val Ala Ala Lys Pro Glu Met Ala Ala Leu Ala Gly Gly Ser Arg
2240                2245                2250

Leu Ala Phe Glu Pro Pro Pro Arg Leu Ser His Leu Pro Val
2255                2260                2265

Ala Ser Ser Ala Ser Thr Val Leu Ser Thr Asn Gly Thr Gly Ala
2270                2275                2280

Met Asn Phe Thr Val Gly Ala Pro Ala Ser Leu Asn Gly Gln Cys
```

| | | | | | | | | | | |
|---|---|---|---|---|---|---|---|---|---|---|
| | | | 2285 | | | 2290 | | | 2295 | |
| Glu | Trp | Leu | Pro | Arg | Leu | Gln | Asn | Gly | Met | Val | Pro | Ser | Gln | Tyr |
| | 2300 | | | | | 2305 | | | | | 2310 | |

Glu Trp Leu Pro Arg Leu Gln Asn Gly Met Val Pro Ser Gln Tyr
    2300                2305                2310

Asn Pro Leu Arg Pro Gly Val Thr Pro Gly Thr Leu Ser Thr Gln
    2315                2320                2325

Ala Ala Gly Leu Gln His Ser Met Met Gly Pro Leu His Ser Ser
    2330                2335                2340

Leu Ser Thr Asn Thr Leu Ser Pro Ile Ile Tyr Gln Gly Leu Pro
    2345                2350                2355

Asn Thr Arg Leu Ala Thr Gln Pro His Leu Val Gln Thr Gln Gln
    2360                2365                2370

Val Gln Pro Gln Asn Leu Gln Leu Gln Pro Gln Asn Leu Gln Pro
    2375                2380                2385

Pro Ser Gln Pro His Leu Ser Val Ser Ser Ala Ala Asn Gly His
    2390                2395                2400

Leu Gly Arg Ser Phe Leu Ser Gly Glu Pro Ser Gln Ala Asp Val
    2405                2410                2415

Gln Pro Leu Gly Pro Ser Ser Leu Pro Val His Thr Ile Leu Pro
    2420                2425                2430

Gln Glu Ser Gln Ala Leu Pro Thr Ser Leu Pro Ser Ser Met Val
    2435                2440                2445

Pro Pro Met Thr Thr Thr Gln Phe Leu Thr Pro Pro Ser Gln His
    2450                2455                2460

Ser Tyr Ser Ser Ser Pro Val Asp Asn Thr Pro Ser His Gln Leu
    2465                2470                2475

Gln Val Pro Glu His Pro Phe Leu Thr Pro Ser Pro Glu Ser Pro
    2480                2485                2490

Asp Gln Trp Ser Ser Ser Ser Pro His Ser Asn Ile Ser Asp Trp
    2495                2500                2505

Ser Glu Gly Ile Ser Ser Pro Pro Thr Thr Met Pro Ser Gln Ile
    2510                2515                2520

Thr His Ile Pro Glu Ala Phe Lys
    2525                2530

<210> SEQ ID NO 3
<211> LENGTH: 316
<212> TYPE: DNA
<213> ORGANISM: Artificial sequence
<220> FEATURE:
<223> OTHER INFORMATION: pTet

<400> SEQUENCE: 3
ggcgatctga cggttcacta aacgagctct gcttatatag gcctcccacc gtacacgcct    60
acctcgacat acgttctcta tcactgatag ggagtaaact cgacatacgt tctctatcac   120
tgatagggat aaactcgaca tacgttctct atcactgata gggagtaaac tcgacatacg   180
ttctctatca ctgataggga gtaaactcga catacgttct ctatcactga tagggagtaa   240
actcgacatc gttctctatc actgataggg agtaaactcg acatacgttc tctatcactg   300
atagggagta aactcg                                                    316

<210> SEQ ID NO 4
<211> LENGTH: 199
<212> TYPE: PRT
<213> ORGANISM: Artificial sequence
<220> FEATURE:
<223> OTHER INFORMATION: puromycin resistance gene

```
<400> SEQUENCE: 4

Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Val Pro Glu Gly Pro Arg Thr Trp Cys
            180                 185                 190

Met Thr Arg Lys Pro Gly Ala
        195

<210> SEQ ID NO 5
<211> LENGTH: 18
<212> TYPE: PRT
<213> ORGANISM: Artificial sequence
<220> FEATURE:
<223> OTHER INFORMATION: 2A

<400> SEQUENCE: 5

Glu Gly Arg Gly Ser Leu Leu Thr Cys Gly Asp Val Glu Glu Asn Pro
1               5                   10                  15

Gly Pro

<210> SEQ ID NO 6
<211> LENGTH: 239
<212> TYPE: PRT
<213> ORGANISM: Artificial sequence
<220> FEATURE:
<223> OTHER INFORMATION: EGFP

<400> SEQUENCE: 6

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60
```

-continued

```
Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 7
<211> LENGTH: 236
<212> TYPE: PRT
<213> ORGANISM: Artificial sequence
<220> FEATURE:
<223> OTHER INFORMATION: mCherry

<400> SEQUENCE: 7

Met Val Ser Lys Gly Glu Glu Asp Asn Met Ala Ile Ile Lys Glu Phe
  1               5                  10                  15

Met Arg Phe Lys Val His Met Glu Gly Ser Val Asn Gly His Glu Phe
                 20                  25                  30

Glu Ile Glu Gly Glu Gly Glu Gly Arg Pro Tyr Glu Gly Thr Gln Thr
             35                  40                  45

Ala Lys Leu Lys Val Thr Lys Gly Gly Pro Leu Pro Phe Ala Trp Asp
         50                  55                  60

Ile Leu Ser Pro Gln Phe Met Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190
```

Gln Leu Pro Gly Ala Tyr Asn Val Asn Ile Lys Leu Asp Ile Thr Ser
    195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 8
<211> LENGTH: 189
<212> TYPE: DNA
<213> ORGANISM: Artificial sequence
<220> FEATURE:
<223> OTHER INFORMATION: SV40 polyplex A

<400> SEQUENCE: 8
ggatcataat cagccatacc acatttgtag aggtttttact tgctttaaaa aacctcccac    60
acctccccct gaacctgaaa cataaaatga atgcaattgt tgttgttaac ttgtttattg   120
cagcttataa tggttacaaa taaagcaata gcatcacaaa tttcacaaat aaagcatttt   180
tttcactgc                                                          189

<210> SEQ ID NO 9
<211> LENGTH: 1265
<212> TYPE: DNA
<213> ORGANISM: Artificial sequence
<220> FEATURE:
<223> OTHER INFORMATION: ef1-alpha promoter

<400> SEQUENCE: 9
aagctttgca aagatggata agttttaaa cagagaggaa tctttgcagc taatggacct    60
tctaggtctt gaaaggagtg ggaattggct ccggtgcccg tcagtgggca gagcgcacat   120
cgcccacagt ccccgagaag ttggggggag ggtcggcaa ttgaaccggt gcctagagaa   180
ggtggcgcgg ggtaaactgg gaaagtgatg tcgtgtactg gctccgcctt tttcccgagg   240
gtgggggaga accgtatata agtgcagtag tcgccgtgaa cgttcttttt cgcaacgggt   300
ttgccgccag aacacaggta agtgccgtgt gtggttcccg cgggcctggc ctctttacgg   360
gttatggccc ttgcgtgcct tgaattactt ccacctggct gcagtacgtg attcttgatc   420
ccgagcttcg ggttggaagt gggtgggaga gttcgaggcc ttgcgcttaa ggagcccctt   480
cgcctcgtgc ttgagttgag gcctggcctg ggcgctgggg ccgccgcgtg cgaatctggt   540
ggcaccttcg cgcctgtctc gctgctttcg ataagtctct agccatttaa aattttttgat   600 gacctgctgc gacgcttttt ttctggcaag atagtcttgt aaatgcgggc caagatctgc   660
acactggtat ttcggttttt ggggccgcgg gcggcgacgg ggcccgtgcg tcccagcgca   720
catgttcggc gaggcgggc ctgcgagcgc ggccaccgag aatcggacgg gggtagtctc   780
aagctggccg gcctgctctg tgcctggcc tcgcgccgcc gtgtatcgcc ccgccctggg   840
cggcaaggct ggcccggtcg gcaccagttg cgtgagcgga agatggccg cttcccggcc   900 ctgctgcagg gagctcaaaa tggaggacgc ggcgctcggg agagcgggcg ggtgagtcac   960
ccacacaaag gaaaagggcc tttccgtcct cagccgtcgc ttcatgtgac tccacgagt  1020 accgggcgcc gtccaggcac ctcgattagt tctcgagctt ttggagtacg tcgtctttag  1080
gttgggggga ggggttttat gcgatggagt ttccccacac tgagtgggtg agactgaag  1140 ttaggccagc ttggcacttg atgtaattct ccttggaatt tgcccttttt gagtttggat  1200
cttggttcat tctcaagcct cagacagtgg ttcaaagttt ttttcttcca tttcaggtgt  1260
cgtga                                                                   1265

<210> SEQ ID NO 10
<211> LENGTH: 248
<212> TYPE: PRT
<213> ORGANISM: Artificial sequence
<220> FEATURE:
<223> OTHER INFORMATION: tTA

<400> SEQUENCE: 10

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Ala Asp Ala Leu Asp Asp Phe Asp Leu Asp Met Leu Pro Ala Asp Ala
    210                 215                 220

Leu Asp Asp Phe Asp Leu Asp Met Leu Pro Ala Asp Ala Leu Asp Asp
225                 230                 235                 240

Phe Asp Leu Asp Met Leu Pro Gly
                245

<210> SEQ ID NO 11
<211> LENGTH: 501
<212> TYPE: DNA
<213> ORGANISM: Artificial sequence
<220> FEATURE:
<223> OTHER INFORMATION: mPGK1 promoter

<400> SEQUENCE: 11
gggtagggga ggcgcttttc ccaaggcagt ctggagcatg cgctttagca gccccgctgg      60
gcacttggcg ctacacaagt ggcctctggc ctcgcacaca ttccacatcc accggtaggc     120
gccaaccggc tccgttcttt ggtggcccct tcgcgccacc ttctactcct ccctagtca     180 ggaagttccc ccccgccccg cagctcgcgt cgtgcaggac gtgacaaatg gaagtagcac     240
gtctcactag tctcgtgcag atggacagca ccgctgagca atggaagcgg gtaggccttt     300

```
ggggcagcgg ccaatagcag ctttgctcct tcgctttctg ggctcagagg ctgggaaggg    360
gtgggtccgg gggcgggctc aggggcgggc tcaggggcgg ggcgggcgcc cgaaggtcct    420
ccggaggccc ggcattctgc acgcttcaaa agcgcacgtc tgccgcgctg ttctcctctt    480
cctcatctcc gggcctttcg a                                              501
```

```
<210> SEQ ID NO 12
<211> LENGTH: 19
<212> TYPE: PRT
<213> ORGANISM: Artificial sequence
<220> FEATURE:
<223> OTHER INFORMATION: CD8alpha signal peptide

<400> SEQUENCE: 12
```

Met Ala Leu Pro Val Thr Ala Leu Leu Leu Pro Leu Ala Leu Leu
1               5                   10                  15

His Ala Ala

```
<210> SEQ ID NO 13
<211> LENGTH: 242
<212> TYPE: PRT
<213> ORGANISM: Artificial sequence
<220> FEATURE:
<223> OTHER INFORMATION: anti-human CD19 single chain antibody

<400> SEQUENCE: 13
```

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 14
<211> LENGTH: 243
<212> TYPE: PRT
<213> ORGANISM: Artificial sequence
<220> FEATURE:
<223> OTHER INFORMATION: anti-human GPC3 single chain antibody

<400> SEQUENCE: 14

```
Asp Val Val Met Thr Gln Ser Pro Leu Ser Leu Pro Val Thr Pro Gly
1               5                   10                  15

Glu Pro Ala Ser Ile Ser Cys Arg Ser Gln Ser Leu Val His Ser
            20                  25                  30

Asn Ala Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Lys Ala Ser Gly Tyr Thr Phe Thr Asp Tyr
145                 150                 155                 160

Glu Met His Trp Val Arg Gln Ala Pro Gly Gln Gly Leu Glu Trp Met
                165                 170                 175

Gly Ala Leu Asp Pro Lys Thr Gly Asp Thr Ala Tyr Ser Gln Lys Phe
            180                 185                 190

Lys Gly Arg Val Thr Leu Thr Ala Asp Glu Ser Thr Ser Thr Ala Tyr
        195                 200                 205

Met Glu Leu Ser Ser Leu Arg Ser Glu Asp Thr Ala Val Tyr Tyr Cys
    210                 215                 220

Thr Arg Phe Tyr Ser Tyr Thr Tyr Trp Gly Gln Gly Thr Leu Val Thr
225                 230                 235                 240

Val Ser Ser
```

<210> SEQ ID NO 15
<211> LENGTH: 557
<212> TYPE: PRT
<213> ORGANISM: Artificial sequence
<220> FEATURE:
<223> OTHER INFORMATION: CD19

<400> SEQUENCE: 15

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
```

```
                50              55              60
Ser Leu Gly Leu Pro Gly Leu Gly Ile His Met Arg Pro Leu Ala Ile
65                      70              75                  80

Trp Leu Phe Ile Phe Asn Val Ser Gln Gln Met Gly Gly Phe Tyr Leu
                    85              90                  95

Cys Gln Pro Gly Pro Pro Ser Glu Lys Ala Trp Gln Pro Gly Trp Thr
                100             105             110

Val Asn Val Glu Gly Ser Gly Glu Leu Phe Arg Trp Asn Val Ser Asp
            115             120             125

Leu Gly Gly Leu Gly Cys Gly Leu Lys Asn Arg Ser Ser Glu Gly Pro
    130             135             140

Ser Ser Pro Ser Gly Lys Leu Met Ser Pro Lys Leu Tyr Val Trp Ala
145             150             155                 160

Lys Asp Arg Pro Glu Ile Trp Glu Gly Glu Pro Pro Cys Leu Pro Pro
                165             170             175

Arg Asp Ser Leu Asn Gln Ser Leu Ser Gln Asp Leu Thr Met Ala Pro
            180             185             190

Gly Ser Thr Leu Trp Leu Ser Cys Gly Val Pro Pro Asp Ser Val Ser
    195             200             205

Arg Gly Pro Leu Ser Trp Thr His Val His Pro Lys Gly Pro Lys Ser
    210             215             220

Leu Leu Ser Leu Glu Leu Lys Asp Asp Arg Pro Ala Arg Asp Met Trp
225             230             235                 240

Val Met Glu Thr Gly Leu Leu Leu Pro Arg Ala Thr Ala Gln Asp Ala
                245             250             255

Gly Lys Tyr Tyr Cys His Arg Gly Asn Leu Thr Met Ser Phe His Leu
                260             265             270

Glu Ile Thr Ala Arg Pro Val Leu Trp His Trp Leu Leu Arg Thr Gly
                275             280             285

Gly Trp Lys Val Ser Ala Val Thr Leu Ala Tyr Leu Ile Phe Cys Leu
    290             295             300

Cys Ser Leu Val Gly Ile Leu His Leu Gln Arg Ala Leu Val Leu Arg
305             310             315                 320

Arg Lys Arg Lys Arg Met Thr Asp Pro Thr Arg Arg Phe Phe Lys Val
                325             330             335

Thr Pro Pro Pro Gly Ser Gly Pro Gln Asn Gln Tyr Gly Asn Val Leu
                340             345             350

Ser Leu Pro Thr Pro Thr Ser Gly Leu Gly Arg Ala Gln Arg Trp Ala
            355             360             365

Ala Gly Leu Gly Gly Thr Ala Pro Ser Tyr Gly Asn Pro Ser Ser Asp
    370             375             380

Val Gln Ala Asp Gly Ala Leu Gly Ser Arg Ser Pro Pro Gly Val Gly
385             390             395                 400

Pro Glu Glu Glu Glu Gly Glu Gly Tyr Glu Glu Pro Asp Ser Glu Glu
                405             410             415

Asp Ser Glu Phe Tyr Glu Asn Asp Ser Asn Leu Gly Gln Asp Gln Leu
            420             425             430

Ser Gln Asp Gly Ser Gly Tyr Glu Asn Pro Glu Asp Glu Pro Leu Gly
    435             440             445

Pro Glu Asp Glu Asp Ser Phe Ser Asn Ala Glu Ser Tyr Glu Asn Glu
    450             455             460

Asp Glu Glu Leu Thr Gln Pro Val Ala Arg Thr Met Asp Phe Leu Ser
465             470             475                 480
```

```
Pro His Gly Ser Ala Trp Asp Pro Ser Arg Glu Ala Thr Ser Leu Ala
            485                 490                 495

Gly Ser Gln Ser Tyr Glu Asp Met Arg Gly Ile Leu Tyr Ala Ala Pro
        500                 505                 510

Gln Leu Arg Ser Ile Arg Gly Gln Pro Gly Pro Asn His Glu Glu Asp
            515                 520                 525

Ala Asp Ser Tyr Glu Asn Met Asp Asn Pro Asp Gly Pro Asp Pro Ala
        530                 535                 540

Trp Gly Gly Gly Arg Met Gly Thr Trp Ser Thr Arg
545                 550                 555

<210> SEQ ID NO 16
<211> LENGTH: 603
<212> TYPE: PRT
<213> ORGANISM: Artificial sequence
<220> FEATURE:
<223> OTHER INFORMATION: GPC3

<400> SEQUENCE: 16

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
            20                  25                  30

Ala Thr Cys His Gln Val Arg Ser Phe Phe Gln Arg Leu Gln Pro Gly
        35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
        275                 280                 285
```

Val Val Glu Ile Asp Lys Tyr Trp Arg Glu Tyr Ile Leu Ser Leu Glu
            290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335

Asn Ala Gly Lys Leu Thr Thr Thr Glu Thr Glu Lys Lys Ile Trp His
            340                 345                 350

Phe Lys Tyr Pro Ile Phe Phe Leu Cys Ile Gly Leu Asp Leu Gln Ile
            355                 360                 365

Gly Lys Leu Cys Ala His Ser Gln Gln Arg Gln Tyr Arg Ser Ala Tyr
            370                 375                 380

Tyr Pro Glu Asp Leu Phe Ile Asp Lys Lys Val Leu Lys Val Ala His
385                 390                 395                 400

Val Glu His Glu Glu Thr Leu Ser Ser Arg Arg Arg Glu Leu Ile Gln
                405                 410                 415

Lys Leu Lys Ser Phe Ile Ser Phe Tyr Ser Ala Leu Pro Gly Tyr Ile
            420                 425                 430

Cys Ser His Ser Pro Val Ala Glu Asn Asp Thr Leu Cys Trp Asn Gly
            435                 440                 445

Gln Glu Leu Val Glu Arg Tyr Ser Gln Lys Ala Ala Arg Asn Gly Met
450                 455                 460

Lys Asn Gln Phe Asn Leu His Glu Leu Lys Met Lys Gly Pro Glu Pro
465                 470                 475                 480

Val Val Ser Gln Ile Ile Asp Lys Leu Lys His Ile Asn Gln Leu Leu
                485                 490                 495

Arg Thr Met Ser Met Pro Lys Gly Arg Val Leu Asp Lys Asn Leu Asp
            500                 505                 510

Glu Glu Gly Phe Glu Ser Gly Asp Cys Gly Asp Asp Glu Asp Glu Cys
            515                 520                 525

Ile Gly Gly Ser Gly Asp Gly Met Ile Lys Val Lys Asn Gln Leu Arg
            530                 535                 540

Phe Leu Ala Glu Leu Ala Tyr Asp Leu Asp Val Asp Asp Ala Pro Gly
545                 550                 555                 560

Asn Ser Gln Gln Ala Thr Pro Lys Asp Asn Glu Ile Ser Thr Phe His
                565                 570                 575

Asn Leu Gly Asn Val His Ser Pro Leu Lys Leu Leu Thr Ser Met Ala
            580                 585                 590

Ile Ser Val Val Cys Phe Phe Leu Val His
            595                 600

<210> SEQ ID NO 17
<211> LENGTH: 233
<212> TYPE: PRT
<213> ORGANISM: Artificial sequence
<220> FEATURE:
<223> OTHER INFORMATION: blue fluorescent protein

<400> SEQUENCE: 17

Met Ser Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
                20                  25                  30

Lys Pro Tyr Glu Gly Thr Gln Thr Met Arg Ile Lys Val Val Glu Gly
            35                  40                  45

Gly Pro Leu Pro Phe Ala Phe Asp Ile Leu Ala Thr Ser Phe Leu Tyr
50                  55                  60

Gly Ser Lys Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Thr Ser
        115                 120                 125

Asn Gly Pro Val Met Gln Lys Leu Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ile Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asn Glu
        195                 200                 205

Thr Tyr Val Glu Gln His Glu Val Ala Val Ala Arg Tyr Cys Asp Leu
    210                 215                 220

Pro Ser Lys Leu Gly His Lys Leu Asn
225                 230

<210> SEQ ID NO 18
<211> LENGTH: 17
<212> TYPE: DNA
<213> ORGANISM: Artificial sequence
<220> FEATURE:
<223> OTHER INFORMATION: primer

<400> SEQUENCE: 18
agtggcctca caggtat                                                17

<210> SEQ ID NO 19
<211> LENGTH: 16
<212> TYPE: DNA
<213> ORGANISM: Artificial sequence
<220> FEATURE:
<223> OTHER INFORMATION: primer

<400> SEQUENCE: 19
acagtcactg agctgc                                                 16

<210> SEQ ID NO 20
<211> LENGTH: 50
<212> TYPE: PRT
<213> ORGANISM: Artificial sequence
<220> FEATURE:
<223> OTHER INFORMATION: transmembrane domain

<400> SEQUENCE: 20

Asn Ala Val Gly Gln Asp Thr Gln Glu Val Ile Val Val Pro His Ser
1               5                   10                  15

Leu Pro Phe Lys Val Val Val Ile Ser Ala Ile Leu Ala Leu Val Val
                20                  25                  30

Leu Thr Ile Ile Ser Leu Ile Ile Leu Ile Met Leu Trp Gln Lys Lys
            35                  40                  45

Pro Arg
    50

<210> SEQ ID NO 21
<211> LENGTH: 395
<212> TYPE: PRT
<213> ORGANISM: Artificial sequence
<220> FEATURE:
<223> OTHER INFORMATION: iCasp9 negative screening system

<400> SEQUENCE: 21

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu Ser Gly Gly Gly
            100                 105                 110

Ser Gly Phe Gly Asp Val Gly Ala Leu Glu Ser Leu Arg Gly Asn Ala
        115                 120                 125

Asp Leu Ala Tyr Ile Leu Ser Met Glu Pro Cys Gly His Cys Leu Ile
    130                 135                 140

Ile Asn Asn Val Asn Phe Cys Arg Glu Ser Gly Leu Arg Thr Arg Thr
145                 150                 155                 160

Gly Ser Asn Ile Asp Cys Glu Lys Leu Arg Arg Arg Phe Ser Ser Leu
                165                 170                 175

His Phe Met Val Glu Val Lys Gly Asp Leu Thr Ala Lys Lys Met Val
            180                 185                 190

Leu Ala Leu Leu Glu Leu Ala Arg Gln Asp His Gly Ala Leu Asp Cys
        195                 200                 205

Cys Val Val Val Ile Leu Ser His Gly Cys Gln Ala Ser His Leu Gln
    210                 215                 220

Phe Pro Gly Ala Val Tyr Gly Thr Asp Gly Cys Pro Val Ser Val Glu
225                 230                 235                 240

Lys Ile Val Asn Ile Phe Asn Gly Thr Ser Cys Pro Ser Leu Gly Gly
                245                 250                 255

Lys Pro Lys Leu Phe Phe Ile Gln Ala Cys Gly Gly Glu Gln Lys Asp
            260                 265                 270

His Gly Phe Glu Val Ala Ser Thr Ser Pro Glu Asp Glu Ser Pro Gly
        275                 280                 285

Ser Asn Pro Glu Pro Asp Ala Thr Pro Phe Gln Glu Gly Leu Arg Thr
    290                 295                 300

Phe Asp Gln Leu Asp Ala Ile Ser Ser Leu Pro Thr Pro Ser Asp Ile
305                 310                 315                 320

Phe Val Ser Tyr Ser Thr Phe Pro Gly Phe Val Ser Trp Arg Asp Pro
                325                 330                 335

Lys Ser Gly Ser Trp Tyr Val Glu Thr Leu Asp Asp Ile Phe Glu Gln
            340                 345                 350

```
Trp Ala His Ser Glu Asp Leu Gln Ser Leu Leu Arg Val Ala Asn
        355                 360                 365

Ala Val Ser Val Lys Gly Ile Tyr Lys Gln Met Pro Gly Cys Phe Asn
    370                 375                 380

Phe Leu Arg Lys Lys Leu Phe Phe Lys Thr Ser
385                 390                 395

<210> SEQ ID NO 22
<211> LENGTH: 256
<212> TYPE: DNA
<213> ORGANISM: Artificial sequence
<220> FEATURE:
<223> OTHER INFORMATION: EFS promoter

<400> SEQUENCE: 22
taggtcttga aaggagtggg aattggctcc ggtgcccgtc agtgggcaga gcgcacatcg      60
cccacagtcc ccgagaagtt ggggggaggg gtcggcaatt gatccggtgc ctagagaagg    120
tggcgcgggg taaactggga aagtgatgtc gtgtactggc tccgcctttt tcccgagggt    180
gggggagaac cgtatataag tgcagtagtc gccgtgaacg ttcttttttcg caacgggttt   240 gccgccagaa cacagg                                                     256

<210> SEQ ID NO 23
<211> LENGTH: 132
<212> TYPE: PRT
<213> ORGANISM: Artificial sequence
<220> FEATURE:
<223> OTHER INFORMATION: blasticidin resistance

<400> SEQUENCE: 23

Met Ala Lys Pro Leu Ser Gln Glu Glu Ser Thr Leu Ile Glu Arg Ala
1               5                   10                  15

Thr Ala Thr Ile Asn Ser Ile Pro Ile Ser Glu Asp Tyr Ser Val Ala
            20                  25                  30

Ser Ala Ala Leu Ser Ser Asp Gly Arg Ile Phe Thr Gly Val Asn Val
        35                  40                  45

Tyr His Phe Thr Gly Gly Pro Cys Ala Glu Leu Val Val Leu Gly Thr
    50                  55                  60

Ala Ala Ala Ala Ala Ala Gly Asn Leu Thr Cys Ile Val Ala Ile Gly
65                  70                  75                  80

Asn Glu Asn Arg Gly Ile Leu Ser Pro Cys Gly Arg Cys Arg Gln Val
                85                  90                  95

Leu Leu Asp Leu His Pro Gly Ile Lys Ala Ile Val Lys Asp Ser Asp
            100                 105                 110

Gly Gln Pro Thr Ala Val Gly Ile Arg Glu Leu Leu Pro Ser Gly Tyr
        115                 120                 125

Val Trp Glu Gly
    130

<210> SEQ ID NO 24
<211> LENGTH: 21
<212> TYPE: DNA
<213> ORGANISM: Artificial sequence
<220> FEATURE:
<223> OTHER INFORMATION: primer

<400> SEQUENCE: 24
gcattctgca cgcttcaaaa g                                                21
```

```
<210> SEQ ID NO 25
<211> LENGTH: 22
<212> TYPE: DNA
<213> ORGANISM: Artificial sequence
<220> FEATURE:
<223> OTHER INFORMATION: primer

<400> SEQUENCE: 25
gaagctgtag tccaggatgt gg                                              22

<210> SEQ ID NO 26
<211> LENGTH: 227
<212> TYPE: PRT
<213> ORGANISM: Artificial sequence
<220> FEATURE:
<223> OTHER INFORMATION: IgG1 constant region

<400> SEQUENCE: 26

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```